(12) United States Patent
Weinstock

(10) Patent No.: US 9,421,370 B2
(45) Date of Patent: Aug. 23, 2016

(54) SYSTEM FOR DIAGNOSING AND TREATMENT OF PANCREAS, OTHER TISSUES AND ORGANS AND OTHER MEDICAL CONDITIONS

(71) Applicant: Ronald J Weinstock, Corona Del Mar, CA (US)

(72) Inventor: Ronald J Weinstock, Corona Del Mar, CA (US)

( * ) Notice: Subject to any disclaimer, the term of this patent is extended or adjusted under 35 U.S.C. 154(b) by 0 days.

(21) Appl. No.: 14/223,701

(22) Filed: Mar. 24, 2014

(65) Prior Publication Data

US 2014/0207018 A1 Jul. 24, 2014

Related U.S. Application Data

(63) Continuation-in-part of application No. 13/065,015, filed on Mar. 11, 2011, now Pat. No. 8,682,448.

(51) Int. Cl.

| | |
|---|---|
| *A61N 1/36* | (2006.01) |
| *A61B 5/053* | (2006.01) |
| *A61N 2/00* | (2006.01) |
| *A61N 2/02* | (2006.01) |
| *A61B 5/04* | (2006.01) |
| *A61B 5/08* | (2006.01) |
| *A61B 5/00* | (2006.01) |

(52) U.S. Cl.
CPC .......... *A61N 1/3606* (2013.01); *A61B 5/04001* (2013.01); *A61B 5/053* (2013.01); *A61B 5/6823* (2013.01); *A61N 2/006* (2013.01); *A61N 2/008* (2013.01); *A61N 2/02* (2013.01); *A61B 5/0531* (2013.01); *A61B 5/08* (2013.01); *A61B 5/425* (2013.01); *A61B 5/4227* (2013.01); *A61B 5/4244* (2013.01); *A61B 5/448* (2013.01)

(58) Field of Classification Search
CPC .. A61B 5/053; A61B 5/04001; A61B 5/0531; A61B 5/425; A61N 1/3606
See application file for complete search history.

(56) References Cited

U.S. PATENT DOCUMENTS

| 5,000,178 A | * | 3/1991 | Griffith | 607/2 |
| 2004/0176805 A1 | * | 9/2004 | Whelan et al. | 607/2 |
| 2006/0074456 A1 | * | 4/2006 | Pyles et al. | 607/40 |
| 2009/0043188 A1 | * | 2/2009 | Rauscher | 600/409 |

* cited by examiner

*Primary Examiner* — Joseph Dietrich
(74) *Attorney, Agent, or Firm* — Melvin K. Silverman

(57) ABSTRACT

An electrotherapeutic treatment system includes a portion of at least one skin or external contact element including an element for measurement of the bioreactance of biologically active neurological points (BANP) of a tissue or organ to be treated, monitoring of electromagnetic parameters received at the points and generating responsive corrective parameters; and a portion of a second electrode for neurologically transmitting bioreactive parameters proximally to a BANP of tissues or organs to be treated, the parameters modifying discrete reactive values responsive to those measured by each of the first or second electrodes responsive to abnormal parameters received from tissues or organs to be treated at or between the BANP.

18 Claims, 19 Drawing Sheets

PEAK CALCIUM CURRENT

INTERNAL FREE $Ca^{2+}$

SYSTEM FOR DIAGNOSING AND TREATMENT OF PANCREAS, OTHER TISSUES AND ORGANS AND OTHER MEDICAL CONDITIONS

CROSS REFERENCE TO RELATED APPLICATION

This application is a continuation-in-part of application Ser. No. 13/065,015, filed Mar. 11, 2011, entitled EMF Probe Configuration for Electro-Modulation of Ionic Channels of Cells and Methods of Use Thereof, which is incorporated herewith in its entirety.

FIELD OF THE INVENTION

The present invention relates to methods for regulating electrical movement of ions in cellular membranes useful to the treatment of diabetes.

BACKGROUND OF THE INVENTION

A movement of electrons, about an atom's nucleus, generates specific ionic interactions and energy emissions, thereby resulting in an ion-based electromagnetic signature pattern of the atom. The electromagnetic signature patterns of multiple atoms are compounded into molecular electromagnetic signature patterns when the multiple atoms combine to form molecules. Similarly, the electromagnetic signature patterns of multiple molecules are compounded into cellular electromagnetic signature patterns when the multiple molecules combine to form cells. Consequently, a tissue, which is composed of multiple cells, has a characteristic electromagnetic signature or image pattern that is a cumulative result of individual electromagnetic signature patterns of the multiple atoms.

In case where the tissue is harmed, injured, diseased, or exhibiting pain, its electromagnetic signature pattern exhibits an abnormality, generally reflective of abnormal ionic cell gradient which leads to abnormal functioning of the tissue, structural damage or even death of the cells. A major cause of this is an abnormal movement of electrons, which abnormally alters the shape and electron field of the atoms, which further alters the membrane structure and ionic balance of the molecule, which in-turn alters the normal functioning and chemistry of the cell, thereby resulting in cell dysfunction, cell damage, and/or cell death.

Diverse research has shown that the cellular functions of the tissues may be affected by magnetic stimuli. Weak magnetic fields exert a variety of biological effects, including causing alterations in cellular ion flux, and consequently affecting the electromagnetic signature pattern of the cells and subsequently, affecting the electromagnetic signature pattern of the tissues formed from those cells.

Conventionally, it is also known that electrical activity in some form is involved in many aspects of human physiology. For example, electrical activity has been measured during the regeneration of bone. In addition, it is well recognized that many cellular responses are dictated by electrical gradients generated in the cell (for example, nerve cells). Therefore, it is possible that exposure of the human body to an electromagnetic field could produce a beneficial physiological response in the body.

There exist several assumptions attending to the mechanism of the effect of low frequency magnetic field exposure on tissues. For example, low frequency magnetic field exposures have been proposed to exert their effect(s) through the induction of electric currents. Generally, research into magnet therapy is divided into two distinct areas, namely, pulsed bioelectric magnetic therapy and fixed magnetic therapy. It is estimated that probably 85 to 90 percent of the scientific literature is on pulsed bioelectric bio-magnetic therapy, and the remainder is on therapy with fixed solid magnets. There exist different theories regarding the essential mechanisms of magnetic therapy, most of which are focused on questions of polarity among other issues. However, fixed magnetic therapy has yet to be widely accepted by the scientific and medical community.

Passive electrical properties of biological tissues are characterized by an impedance, the value of which is determined by the capacitance, inductance and conductance of the corresponding of the tissue of interest. The active component of electric conductivity at low frequencies depends, in the main, on the amount and the electrolyte composition of the intercellular liquid; at high frequencies an additional contribution is made by the electrical conductivity of cells. Since the resistance of cells is series-connected with that of the cellular membrane, there occurs a frequency dispersion of the electric conductivity of biological tissues. Having high dielectric property and an extremely small thickness, bilayer cell lipid membranes are characterized by a large value of charge capacity of the membranes and, consequently, the capacitance properties of biological tissues are due to the considerable polarization capacity of the dielectric of the membrane which depends on its relative permittivity. At high frequencies polarization mechanisms become switched-off with slowing-down of the relaxation time; therefore, with an increase in the frequency, the capacity of tissues to retain charge decreases.

In the range of low frequencies, the impedance of tissues is determined, mainly by their resistive properties. To this range there pertain tissues having a high electric conductivity (nerve tissue). At the range of medium frequencies are tissues whose electrical properties are determined by the resistive and capacitive properties. At most frequencies the character of the electrical properties of tissues is capacitative (membranes, lipids). Slowed-down polarization mechanisms in this range of frequencies may involve considerable dielectric losses in the tissues. Therefore, the living cell can be represented as an oscillatory circuit with a capacitance and a resistance, the membrane capacitance being determined by free-radical reactions and by the antioxidant protection system, whereas the resistance is determined by enzymatic oxidation in or at the membrane wall.

Generation of electromagnetic field pulses from units to tens of Hz is a characteristic feature of normal functioning of various human organs. It is not only the cell that can be represented as an oscillatory circuit, but higher organization levels of living matter as well: tissues and organs with different predominance of glucose oxidation pathways, systems of organs and the entire organism as an inductively equilibrium system of oscillatory circuits. Such an organ as the liver comprises both glucose oxidation pathways in equal proportions, which makes it the key organ in the system regulating the capacitance and inductance of the organism. The blood circulation system per se is also a state of closed conductors, from the loops of capillaries to the greater and lesser aspects of circulation. Differences in the impedances of venous and arterial blood provide conditions for the mutual influence of organs. The electric properties of blood are determined by the amount of hemoglobin, oxygen and other cyclic compounds in it, by its protein-electrolytic composition, and by the circulation rate.

Therefore, an electric field considered within the framework of classical electrodynamics can integrate the functioning of the whole organism, by creating and preserving the specialization of different tissues. The blood circulation system being a major intermediary through which regulation is effected.

The philosophy of ancient Chinese medicine regards the organism as a single whole, in which each part is subordinated to this whole, and the whole depends on each part. Although explained in the Chinese scientific terms of 5000 years ago, ancient Chinese medical science in many ways mirrors today's understanding of biophysics and bio-physiology. The energy ch'i, divided into yang and yin principles in their constant interaction and dynamic balance, fully corresponds to the integration basis of the electromagnetic field of an oscillatory circuit, wherein the ch'i is replaced by inductance and the yang and the yin are represented as a capacitor and a resistor. Then, biologically active neurological points ("BANP") represent additional energy regulation sources in the form of a nerve coiled around a nerve core in which an electromotive force will be generated on excitation of the nerve or weaken on removal of the excitation from the nerve, and vice versa.

The electromagnetic oscillations which exist inside every living organism depend only in part on the oscillations existing outside the organism. Though natural oscillations of the organism are excited by the oscillations of external magnetic fields, these natural oscillations then originate in the organism again, in a specific form. Each organ and each cell has its specific spectrum of oscillations, its specific characteristics of these oscillations (form and kind, as well as frequency). Maintenance of these oscillations depends on the "Q-factor" of the LC resonators of the cell, organ, tissue or organism as a whole. If the "Q-factor" of the resonator is disturbed or absent, incoherent, inadequate, pathological electromagnetic oscillations may arise. When the mechanism of self-regulation and sanitation, existing in the organism, proves to be unable to properly control these oscillations, the result will be a disease with the type of disease being determined by the type of cell, cell system, organ or organ system being effected.

Specific responses of the human organism to the action of an artificial electromagnetic field have been detected when passing over a weak low-frequency field (when the intensities of a field induced inside the organism were essentially smaller than 0.1 V/cm$^2$). It should be noted that when the intensity of an external field is on the order of 10 V/m, the values of the field induced inside the organism practically cannot be measured experimentally. Physiological processes are controlled by ultra-low waves, i.e., by processes on the order of 1 Hz, with the specific resistance of nerve tissues of about 300 ohms/cm$^2$, when considering the effects produced on humans by artificial and natural low-frequency electromagnetic fields in the range from 0.1 to 100 Hz.

In accordance with the principle of reciprocity of antennas, any structure performing reception of electromagnetic fields is also capable of radiating in the same frequency range. Therefore, the object of one investigation was to find electric signals within the range of low frequencies from 0.1 to 100 Hz at biologically active neurological points (BANP) of the body. Low-frequency electric signals have been detected in said zones. Those signals had maximum amplitude values at some discrete frequencies in the range of from a few Hz to tens of Hz. Furthermore, weak low-frequency radiations of electromagnetic fields in the range of from 0.1 to 100 Hz, also having a discrete spectrum in the range of tens Hz, were recorded in above the body surface in these zones. It was established that as a probe is displaced from the BAP, the amplitudes of received signals decrease sharply; the character of the spatial distribution of the signals in their zone is anisotropic. In neutral portions of the body the character of observed signals was noise-like, and their amplitude was 5 to 10 times smaller than in biologically active neural points (BANP).

It is also well known that the concept of pulsed electromagnetic effects was first observed by the renowned scientist Michael Faraday in 1831. Faraday demonstrated that time varying magnetic fields have the potential to induce current in a conductive object. Faraday found that by passing strong electric current through a coil of wire, he was able to produce electrical pulses having magnetic effects. Such pulsed magnetic stimulus was also able to induce the flow of current in a nearby electrically conductive body.

In the years following the discoveries of Faraday, pulsed electromagnetic stimulators have found application in certain areas of scientific investigation. For example, in 1965, the scientists Bickford and Freming demonstrated the use of electromagnetic stimulation to induce conduction within nerves of the face. Later, in 1982, Poison et al., as disclosed in U.S. Pat. No. 5,766,124 produced a device capable of stimulating peripheral nerves of the body. This device was able to stimulate peripheral nerves of the body sufficiently to cause muscle activity, recording the first evoked potentials from electromagnetic stimulation. Moreover, the application of extremely low frequency (less than 100 hertz) electromagnetic signals has beneficial therapeutic effects. See, for example, the paper "Therapeutic Aspects of Electromagnetic Fields for Soft-Tissue Healing" by B. F. Siskin and J. Walker, 1995 published in *Electromagnetic Fields: Biological Interactions and Mechanisms*, M. Blank editor, Advances in Chemistry Series 250, American Chemical Society, Washington D.C., pages 277-285, which at pages 280-81 discusses the effects on ligaments, tendons, and muscles of fields up to 1000 Gauss using EMF pulse trains of 1 to 500 Hz, over periods of up to ten weeks.

Further, as discussed previously, bone material may also be treated using electromagnetic and/or vibrational energies. Subsequently, pulsing electromagnetic fields have been widely used by orthopedic physicians to stimulate the healing of fracture non-unions. See, e.g., the 1995 article by Bassett entitled "Bioelectromagnetics in the Service of Medicine" published in *Electromagnet Fields Biological Interactions and Mechanisms*, M. Blank editor, Advances in Chemistry Series 250, American Chemical Society, Washington D.C., pp. 261-275. One of the earliest practical applications of electromagnetic stimulating technology took the form of a bone growth stimulator a device that employed low frequency pulsed electromagnetic fields (PEMF) to stimulate bone repair.

In the past, pulsed electromagnetic stimulation devices have taken a number of different forms in attempts to treat various medical conditions. Generally, these different forms have resulted in two broad categories of coil arrangements for the generation of PEMFs: (1) planar or semi-planar designs with tightly wound coils, and (2) solenoid coils. Flat, wound coils create electromagnetic fields that degrade rapidly over a short distance as they pulse away from the inducing signal.

Prior art known to the inventor includes patent to Dissing et al, namely, U.S. Pat. No. 6,561,968, entitled "Method And An Apparatus For Stimulating/Modulating Biochemical Processes Using Pulsed Electromagnetic Fields," which discloses stimulating and/or modulating growth and differentiation in biological or plant tissue, seeds, plants, and microorganisms. Dissing discusses an apparatus including a pulse generator and a plurality of coils, in which pulsed currents cause fluctuating magnetic fields in a predetermined region holding the material to be stimulated. However, the apparatus is large and cumbersome and does not readily lend itself to private personal use.

Blackwell holds U.S. Pat. No. 6,186,941 entitled "Magnetic Coil for Pulsed Electromagnetic Field", which teaches use of portable PEMF coils for treatment of injuries in a patient.

U.S. Pat. No. 5,518,496 to McLeod relates to an apparatus and a method for regulating the growth of living tissue. The apparatus includes a deformable magnetic field generator and a magnetic field detector for producing a controlled, fluctuating, directionally oriented magnetic field parallel to a predetermined axis projecting through the target tissue.

U.S. Pat. No. 7,175,587 to Gordon relates to an apparatus and method for applying pulsed electromagnetic therapy to humans and animals. Gordon teaches a straight wire element that is employed to generate the magnetic field, and, a power and timer circuit that supplies current pulses that approximate square pulses in form, so that the straight wire element generates magnetic pulses having rapid rise and fall times.

Conventionally, techniques which have been used to treat injuries using PEMF include the use of Helmholtz and toroidal coils to deliver PEMF. Such methods and apparatuses generally suffer from various disadvantages. For example, Helmholtz coils suffer from field inhomogeneity and field dropoffs in certain zones (e.g., the field drops to zero near the center of the coil). Toroidal coils are inefficient and have relatively weak field strength. Additionally, known methods of PEMF treatment have problems associated with system complexity, large size and weight, long treatment times, weak PEMF strength and low efficiencies in promoting healing. Current devices and methods of PEMF treatment further fail to provide adequate mobility during treatment.

Recent developments in molecular cell biology have confirmed the principles reflected in the above material. For example, Jiang et al, Rockfeller University, 2002, states that Ion channels exhibit two essential biophysical properties: (a) selective ion conduction, and b) the ability to gate-open in response to an appropriate stimulus. Two general categories of ion channel gating are defined by the initiating stimulus: (a) ligand binding (neurotransmitter—or second-messenger-gated channels) and (b) membrane voltage (voltage-gated channels). The structural basis of ligand gating in a K+channel is that it opens in response to intracellular $Ca^{2+}$. Jiang et al reports they have cloned, expressed, and analyzed electrical properties, and determined the crystal structure of a K+channel from *methanobacterium thermoautotrophicum* in the (Ca2+) bound, opened state and that eight RCK domains (regulators of K+conductance) form a gating ring at the intracellular membrane surface. The gating ring uses the free energy of Ca2+ binding to perform mechanical work to open the pore.

The molecular characterization of the neuronal calcium channel has been studied by Perez-Ryes. *Nature* 1998, 391: 896.

The role of biological ions are mediators of the cellular activity is well established. Various technologies exist for controlling movement of ionic species across the membrane of living cell. Herein, the effectuation of such movement at a distance, using axonic pathways of the nervous system, is explored with specific reference to the spinal cord relative to the pancreas.

Prior art known to the inventor of an electrotherapeutic treatment of diabetes is reflected in U.S. Patent Application Publication U.S. 2004/0249416 to Yun et al entitled Treatment of Conditions thru Electrical Modulation of the Autonomic Nervous System. The inventor's method and systems differ greatly from the work of Yun et al; Garcia et al of U.S. Pat. No. 8,457,745 (2013); and Rezai et al, U.S. Pat. No. 8,583,229 (2013).

SUMMARY OF THE INVENTION

An electrotherapeutic treatment system includes at least one skin contact element including a first electrode for measurement of bioreactance at biologically active neurological points (BANP) of a tissue or organ to be treated, including monitoring of electromagnetic parameters received at said points and means for generating corrective parameters responsive to those measured; and a second electrode, situated on the abdomen proximally to a tissue or organ to be treated, for neurologically transmitting bioreactive parameters at said BANP of said tissues or organs, said parameters modifying discrete reactive values responsive to those measured by said first and second electrodes responsive to abnormal parameters received from tissues or organs to be treated at said BANP.

It is an object of the invention to employ discreet electrical and magnetic waveforms for the analysis and treatment of abnormalities of cells of organs in the human body.

It is another object to provide a system to analyze, separate and digitize EM patterns of cells of specific tissues for purposes of treatment thereof.

It is further object of the invention to normalize and correct complex electromagnetic wave abnormal electrical and/or magnetic field spectra utilizing inductive sensors and electrodes means to apply therapeutic EM patterns.

It is a yet further object to provide a system of the above type in which a received EM wave pattern is measured at a BANP (biologically active neurological point) or trigger point, at or near a tissue dysfunction or pain site, and to apply counter-pattern to said site to realign unstable, shifted and depressed patterns associated with the membrane and membrane dysfunction of cells resultant of abnormal or pain conditions.

In accordance with another aspect of the present invention, there is provided a method, which employs an EMF probe assembly for treating abnormalities of cells in the human body. The method may further comprise the step of treating a damaged or a particular dysfunctional cellular area or membranes thereof.

It is accordingly an object of the invention to provide an electrotherapeutic system of treatment of a broad range of medical conditions.

It is another object to enhance activity of beta cells of the human pancreas to preclude onset of diabetes-like symptoms or reverse the same.

It is a further object of the invention to monitor selected electromagnetic wave patterns within the T6 to T12, and related neural off-shoots and vertebrae, to provide an early or diagnosis of, or susceptibility to, diabetes and treatment thereof.

It is also a further object of the invention to monitor selected electromagnetic wave patterns within the C-1 to coccysxal nerve, and related neural off-shoots and vertebrae, to provide an early diagnosis of, or susceptibility to, various medical conditions, organ and organ system dysfunctions, and diseases and treatments thereof.

The above and yet other objects and advantages of the present invention will become apparent from the hereinafter set forth Brief Description of the Drawing, Detained Description of the Invention and Claims appended herewith.

DETAILED DESCRIPTION OF THE INVENTION

As is well-known, the sympathetic nervous system (SNS) is a branch of the autonomic nervous system and of the central nervous system (CNS) and is related to the parasympathetic nervous system (PNS).

The SNS is active at a so-called basal level and becomes active during times of stress. As such, this stress response is termed the fight-or-flight response. The SNS operates through a series of interconnected neurons. Sympathetic neurons are frequently considered part of the PNS, although many lie within the CNS. Sympathetic neurons of the spinal cord are of course part of the CNS, and communicate with peripheral sympathetic neurons through a series of sympathetic ganglia. For purposes of the present invention, the CNS may be viewed (see FIG. 31) as consisting of a spinal cord 10 and a sympathetic trunk 12 thereof.

Figure 31:
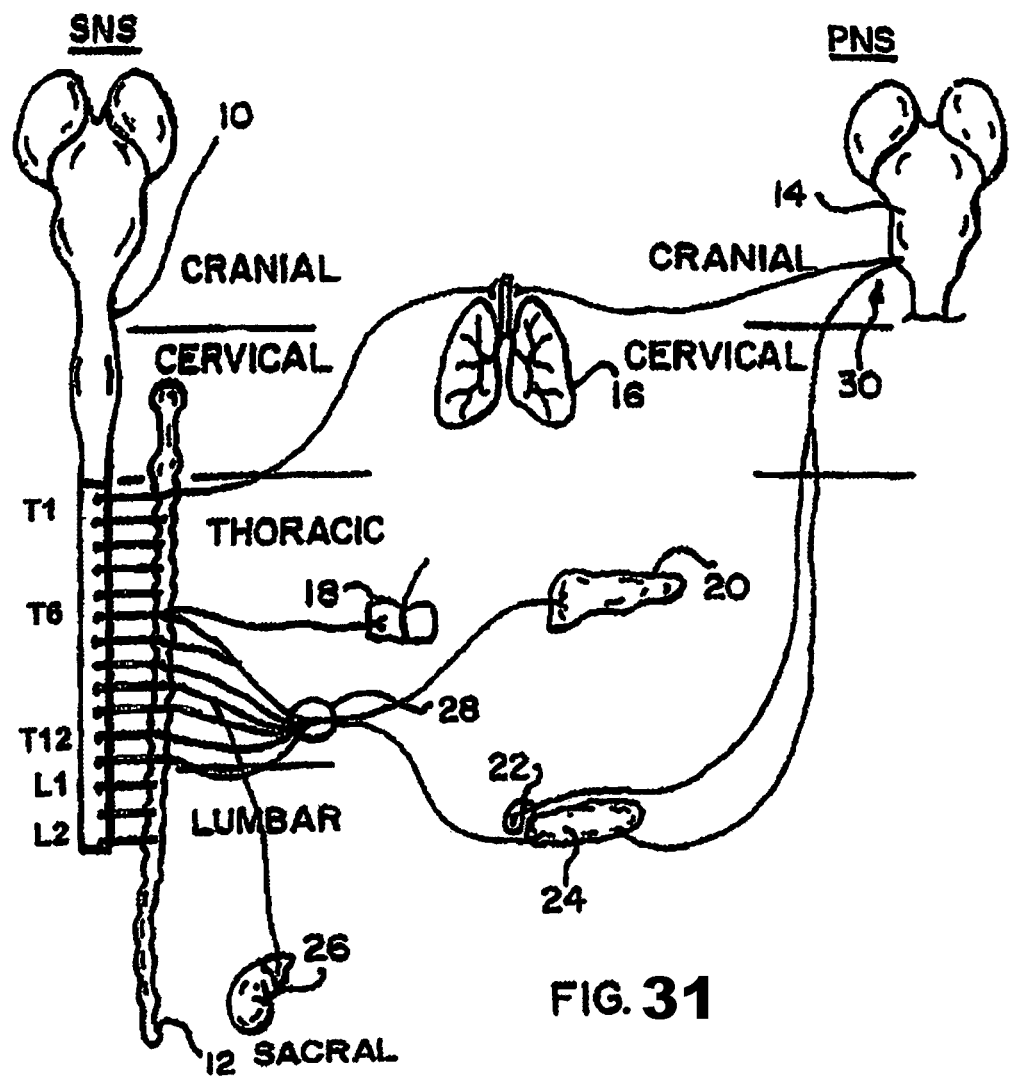
FIG. 31 is a schematic view of the spinal cord and its sympathetic and parasympathetic relation to internal organs of the body.

The PNS is shown to the right of FIG. 31 as numeral 14. The PNS is considered an automatic regulation system, that is, one that operates without the intervention of conscious thought. As such, fibers of the PNS innervate tissues in almost every organ system, providing at least some regulatory function to areas as diverse as the diameter of the eye, gut motility, and urinary output. For purposes of the present invention, many organs are regulated by the SNS including lung 16, hair follicles 18, liver 20, gall bladder 22, pancreas 24, adrenal glands 26, and hypertension generally. As may be noted in FIG. 31, many neurons of nerves of the SNS of interest originate in the thoracic vertebrae of the spinal cord and pass through sympathetic trunk 12 thereof. This is known as the thoracolumbar outflow of the SNS. Therein, axons of these nerves leave the spinal cord through anterior outlets/routes thereof of the sympathetic trunk 12 and, certain groups thereof, including the groups emanating from thoracic vertebrae T6 through T12 as well as to the coccysx reach celiac ganglion 28 before dispersing to various internal organs in the thoracic region of the body including pancreas 24. From these internal organs occurs a flow of axons of these respective nerves to the base of the PNS at the vagus nerve 30 shown in FIG. 31.

To reach target organs and glands, axons must travel long distances in the body, and to accomplish this, many axons relay their message to a second cell through synaptic transmission. This entails the use of a neuro-transmitter across what is termed the synaptic cleft which activates further cells known as post-synaptic cells. Therefrom, the message is carried to the final destination in the target organ.

Messages travel through the SNS in a bi-directional fashion. That is, so-called efferent messages can trigger changes in different parts of the body simultaneously to further the above referenced fight-or-flight response function of the SNS. It is noted that the PNS, in distinction to the CNS, controls actions that can be summarized as rest-and-digest, as opposed to the fight-or-flight effects of the SNS. Therefore, many functions of the internal organs are controlled by the PNS in that such actions do not require immediate reaction, as do those of the SNS. Included within these is the control of the gall bladder 22 and pancreas 24 by the SNS, as may be noted in FIG. 31.

It may thereby be appreciated that the autonomic nervous system includes both said SNS and PNS divisions which, collectively, regulate the body's visceral organs, their nerves and tissues of various types. The SNS and PNS must, of necessity, operate in tandem to create synergistic effects that are not merely an "on" or "off" function but which can better be described as a continuum of effect depending upon how vigorously each division must execute its function in response to given conditions. The PNS often operates through what are known as parasympathetic ganglia and includes so-called terminal ganglia and intramural ganglia which lie near the organs which they innervate, this inclusive of the pancreas.

In summary, a change of axon activity within an internal organ is measurable at one or more of the T6 through T12 thoracic locations and C1 to coccysx locations of the SNS and, in principle, also at the vagus nerve 30 of the PNS, above described.

Figure 1:
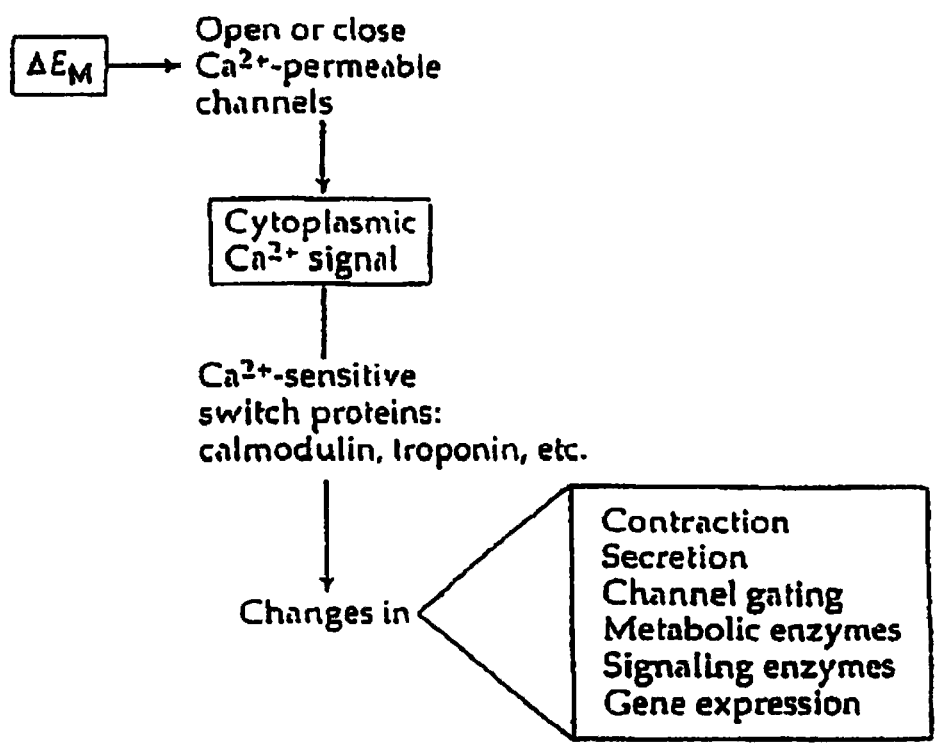
FIG. 1 is a flow diagram showing cytoplasmic calcium and other changes that occur when membrane potential changes are sensed by a cell.

The inventor, in clinical studies, has noticed that a dysfunction of a given internal organ can be recognized by a retardation of signal strength and stability within the neurons at the T6 through T12, and C1 to coccysx nerve locations of the spinal cord. More particularly, in persons suffering from diabetes, I have found weakness and instability of neuro-transmitted signals which would normally pass from pancreas 24, through celiac ganglien 28 and to vertebrae T6 to T12 of the spinal cord. See FIG. 1.

It is believed that appropriate measurements, if taken, at vagus nerve 30 of the PNS would show a similar retardation or instability of otherwise normal signal reaching the cranial base through the nerves of the PNS. Responsive to the above observations, I propose treatment of this instability of the internal organs, inclusive of the pancreas, by the application of appropriate electromagnetic signals through C1 to coccysx nerve, T6 to T12 of the SNS, and at the vagus nerve of the PNS, as a means of treating reduced pancreatic function.

That cells of the human body are acutely responsive to electrical and electromagnetic stimulation through neurotransmitters and otherwise, has long been established by research in the area. Calcium has been determined to be the final transmitter of electrical signals to the cytoplasm of human cells. More particularly, changes in cell membrane potential are sensed by numerous calcium-sensing proteins of cell membrane which determine whether to open or close responsive to a charge carrying elements, in this case, the calcium anion $Ca^{2+}$. This is shown conceptually in FIG. 1 which shows the electrical call to action of a cell upon its sensing of a voltage gradient carried or created by a calcium anion. Stated otherwise, calcium ions transduce electrical signals to the cells through what are termed voltage-gated calcium channels (see Hille, "Ion Channels of Excitable Membranes," 3 Ed., 2001, Chap. 4). It is now recognized that electrical signaling of voltage-gated channels (of which there are many categories) of human cell membranes is controlled by intracellular free calcium (and other) ionic concentrations, and that electrical signals are modulated by the flow of calcium anions into cytoplasm from the external medium or from intra cellular stores.

One well-studied calcium dependent process is the secretion of neuro-transmitters at nerve terminals. See Hille, page 104 thereof. Within the presynaptic terminal of every chemical synapse, there are membrane-bounded vesicular-containing high concentrations of neurotransmitter molecules of various types. When such an action potential engages a neurotransmitter, the membranes having one or more of these vesicules in their surface membrane, release a group of neuro-transmitters into the cellular space. This is conceptually shown in FIG. 2. In the pancreas, there exist so-called pancreatic acinar cells which contain zymogen granules which assist in cellular functions thereof.

Figure 2:
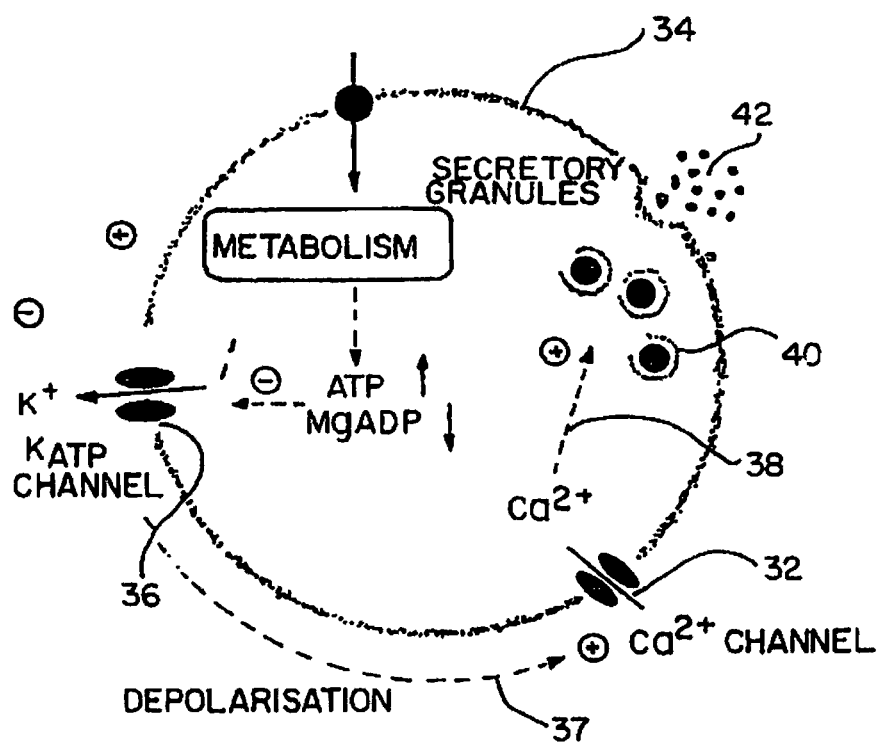
FIG. 2 is a diagrammatic view showing the role that the $Ca^{2+}$ and $K^+$ channels play in insulin secretion.
Figure 3:
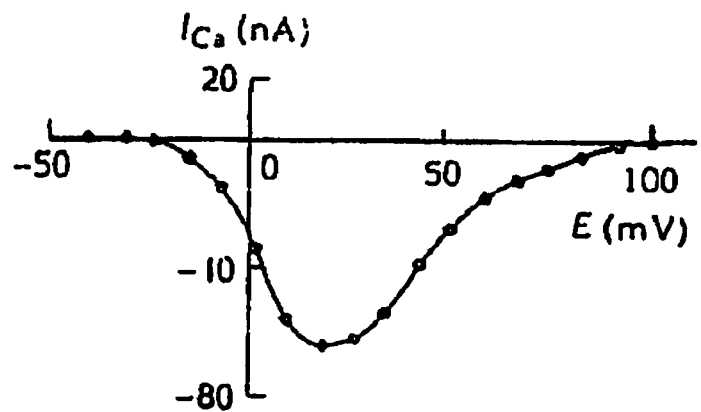
FIG. 3 is a graph showing the relationship between cell membrane potential, and calcium ion related current flow in a human cell.

Normally stimulated secretion from nerve terminal of most excitable cells require the extracellular calcium anions $Ca^{2+}$ pass thru ionic channels of the cell. The above is shown at a cellular level in the schematic view of FIG. 2 which shows the calcium ionic channel 32 of cell 34 as well as the egress of a potassium anion through a so-called KATP channel 36 when a calcium anion enters the cell. This process triggers a variety of functions which relate to insulin secretion. Lack of sufficient secretion is of course the primary cause of diabetes as it is broadly understood. FIG. 2 therefore illustrates the current model of insulin secretion (Ashcroft, "Ion Channels and Disease," 2000, p. 155).

In summary, FIG. 2 indicates that when plasma glucose levels rise, glucose uptake and metabolism by the pancreatic beta cells is enhanced, producing an increase in the intracellular ATP which is a cellular energy source. These changes act in concert to close calcium channels 36 in the beta-cell membrane because ATP inhibits, whereas MgADP (shown in FIG. 2) activates, calcium ion channel activity. In that calcium channel activity determines the beta cell resting potential, its closure causes a membrane depolarization 37 that activates voltage-gated calcium anion channels 32, increasing calcium influx and stimulating insulin release. Insufficient charge upon intracellular calcium may, it is believed, be one cause of inhibition of the above-described normal metabolic process of the pancreatic beta cells. In other words, if intracellular calcium, or its relevant neurotransmitters, lack sufficient charge, insufficient electrical energy 38 is provided to secretory granules 40 sufficient to effect insulin release 42, that is necessary to metabolize glucose 44.

Another view of insulin secretion is that, by blockage of potassium ion channels 36, sufficient charge can be sustained within the cell to maintain normal function of secretory granules 40 and therefore of insulin release 42. Therapeutic drugs which seek to so modulate insulin secretion by control of the potassium channels are sulphonylureaus and diazoxide.

In summary, when blood glucose 44 rises, the uptake thereof is increased by the action of the calcium anions $Ca^{2+}$ entering cell 34. Aspects of this metabolism cause the potassium ATP channels 36 to close which results in membrane polarization 37, a change of voltage potential at calcium ion channels 32, and an increase in cytoplasmic anionic calcium that triggers the function of insulin secretory granules 40. It is therefore desirable to regulate calcium channel activity by maintaining a low level of blood glucose. This requires that an adequate molarity of $Ca^{2+}$ exist in the beta cells of the pancreas.

Figure 4:
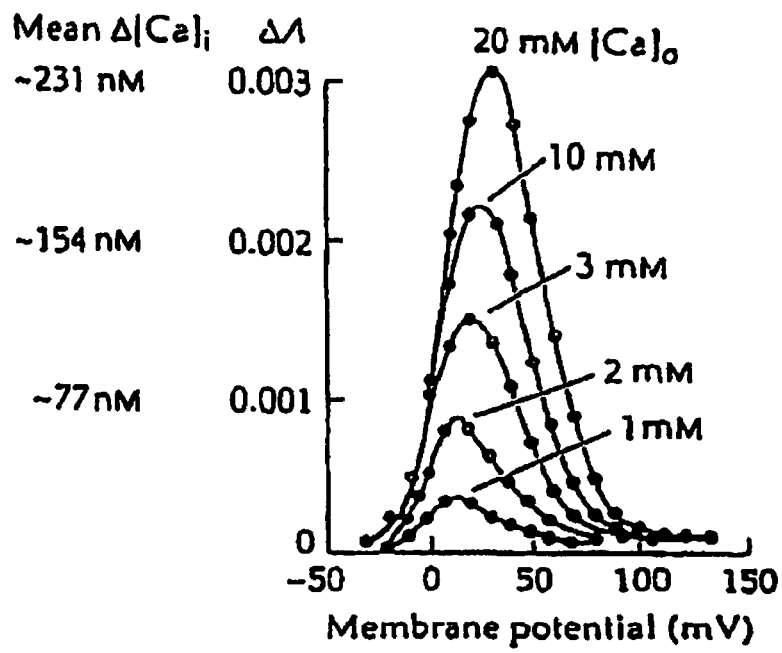
FIG. 4 is a graph showing the relationship between cell membrane potential and concentration of free calcium ions within a cell.
Figure 5:
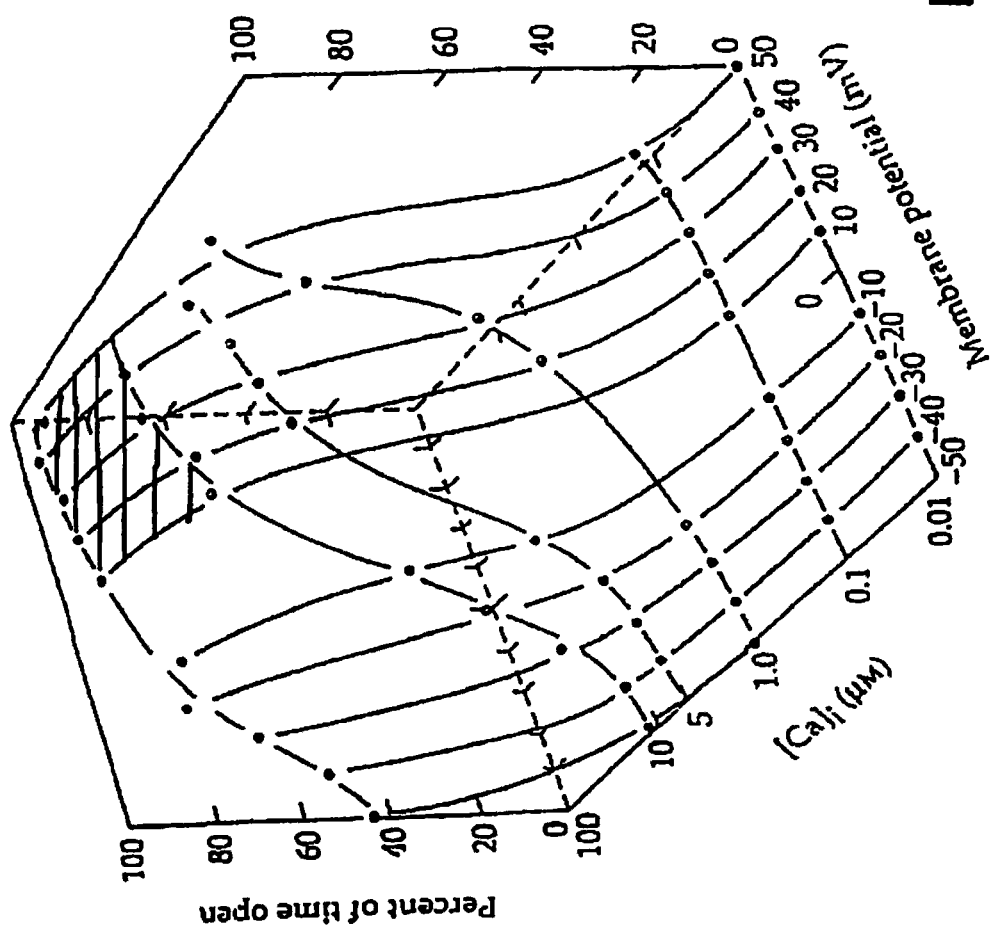
FIG. 5 is a three-dimensional graph showing the relationship between cell membrane potential, calcium ion related current flow into the, cell and percent of time that calcium gated channels of the cell are open.

The relation of the offset of ionic calcium on membrane potential of the cell, ionic current flow within the cell, and molarity of calcium within the cell are shown in FIGS. 4 and 5 respectively. FIG. 5 indicates that the percent of time of calcium channel opening as a function of membrane potential and calcium molarity within the intracellular media. Stated otherwise, an increase in membrane potential will increase the time that voltage-gated ionic channels of the cell are open. In view of the above, it appears an appropriate increase in ionic calcium within beta cells of the pancreas will bring about an increase in insulin release if supported by a sufficiency of the membrane potential. The cross-hatched area at the top of the graph of FIG. 5 represents a confluence of parameters most beneficial to the health of the cell.

In view of the above, the inventor proposes the delivery of such enhanced membrane potential to beta cells of the pancreas through the SNS and/or PNS, as above described with reference to FIG. 31, by the application of appropriate electromagnetic signals at the T6 through T12 thoracic vertebrae and, in the case of the PNS, through vagus nerve 30.

Potential choices of appropriate signals may be frequency critical as has been set forth by Sandblom and George, "Frequency Response in Resonance Behavior of Ionic Channel Currents Modulated by AC Fields" 1993, who indicate that ionic channel currents calculated are frequency-dependent, describing the rates of transports of ions through channels. "Liboff, et al, has proposed an optimum fluctuating magnetic field frequency for regulating transport frequency regulating transport across ionic membrane. See U.S. Pat. No. 5,160,591 (1992).

It is anticipated that, in one embodiment, appropriate electrical magnetic or electro-magnetic stimulation can be furnished to every vertebrae and vertebral nerve outlet from the C1 vertebrae throughout all of the thoracic and lumbar vertebras and including the sacreal vertebras and below to the coccysx and it's nerve outlets by the use of probes (see FIG. 32), and that these would include both low and high frequency fields, inclusive of. AC and DC, with AC upon a DC carrier or, as taught by Liboff above, using a Helmholz Coil to produce cyclotronic magnetic fields that are imparted to tissue or nerves of interest.

Recent developments in molecular cell biology have confirmed the principles reflected in FIGS. 2-5 above. For example, Jiang et al, Rockfeller University, 2002, states: Ion channels exhibit two essential biophysical properties: a) selective ion conduction, and b) the ability to gate-open in response to an appropriate stimulus. Two general categories of ion channel gating are defined by the initiating stimulus: ligand binding (neurotransmitter—or second-messenger-gated channels) or membrane voltage (voltage-gated channels), per FIGS. 4-6. The structural basis of ligand gating in a K+ channel is that it opens in response to intracellular $Ca^{2+}$. Jiang author reports he has they cloned, expressed, and analysed electrical properties, and determined the crystal structure of a K+ channel from *methanobacterium thermoautotrophicum* in the (Ca2+) bound, opened state and that eight RCK domains (regulators of K+ conductance) form a gating ring at the intracellular membrane surface. The gating ring uses the free energy of Ca2+ binding to perform mechanical work to open the pore.

Many forms of cellular dysfunction have been related to the electrical call to action of cells upon sensing of the voltage gradient, the cell membrane required to open the ionic channels. As such, electrical signals are modulated by the flow of calcium anions from and to the external medium thus affecting intra-cellular storage. Correction of any malfunction in the ability of the cell to provide a proper signal is summarized in FIG. 1 and shown schematically in FIG. 2. The present invention thereby provides necessary electrical and electromagnetic parameters, as summarized in FIGS. 3-5, and taught in my U.S. Pat. No. 7,801,585 (2010) necessary to optimize the flow of calcium anions to thereby restore normal function of dysfunctional cells within a given tissue. It is to be appreciated that other anions and their channels, e.g., potassium or sodium ion and channels, may be associated with a given dysfunction.

FIGS. 6 to 12 illustrate the general appearance of probe 107 used in the practice of the inventive method of treatment of abnormalities of soft tissue nerves and organ cells in the human body. The handle of probe 107 may be formed of a polymeric material such as ABS or any non-conductive equivalent thereof. Provided therein are preferably identical ferrite cores 101 and 108 around which are wound induction coils 102 and 112. Their magnetic fields may be axially variable if a pivot point for the middle of the axis of the cord is provided. The axial magnetic fields resultant of these structures as shown as arrows B1 and B4 in FIGS. 6 and 8, each of which however produces oval-like peripheral outer fields B2 and B5 as well as inner fields B3 and B6 which bend in the direction of a central spherical probe 110 of the structure. The direction of B4 is opposite to that of B1 because the respective directions of current flow therein are opposite. Said induction coils 102 and 112 will preferably produce an inductance and associated axial magnetic fields in a range of 0.5 to 1000 milliGauss. The lateral magnetic fields B2 and B5 associated with the coils and their ferrite cores would typically fall in a similar milliGauss range. Coils 102 and 112 are powered by a current at a frequency a range of 1 to 120 G Hertz, but the current therein flow in opposite directions. See FIG. 8.

The axially disposed spherical probe 110 produces an electromagnetic pulse train Ep/112 and magnetic pulsed field B7, schematically shown as arrows and loops in FIG. 6 and as it would appear on an oscilloscope in FIG. 11, as set forth in the text below. These AC pulses generate an associated spiral magnetic field B7 shown in FIG. 6. The primary lines of pulsed magnetic field B7 are at right angles to the primary lines of magnetic flux B1 to B4 associated with the coils 102 and 112 above described. The fact that electrical pulse 112 is projected at a right angle, particularly to fields B1 and B4, will result in a so-called ExB vector force which contributes to the therapeutic effects described herein.

Spherical probe 110 therefore normally emits a complex pulsed EM wave into the treated tissue having, on one plane, the general pulse geometry shown in FIGS. 17 and 19, as explained below. For simplicity, aspects of the electrical signal 112 caused by the above-referenced cross-vector effect are not shown. However, it is to be appreciated that the waveforms of FIG. 11 include a magnetic component which projects transversely to the plane of the image shown in FIG. 11 prior to and during response from the tissue.

A molecular manifestation of a disease would be seen in the small amplitude sinusoidal components of the signal. At that level, disease appears as a distortion in the normal electron path or of the valance shell geometry of the molecule. Biologic molecules may be very large and complex. The lower energy effects of frequency, phase, amplitude and waveform of the various E and B induced fields function to correct these distortions of geometry of molecules and cell membranes of the target cells. As such, concurrent use of electrical and magnetic fields, inclusive of important interactions therebetween, maximize the healing function.

Figure 8:
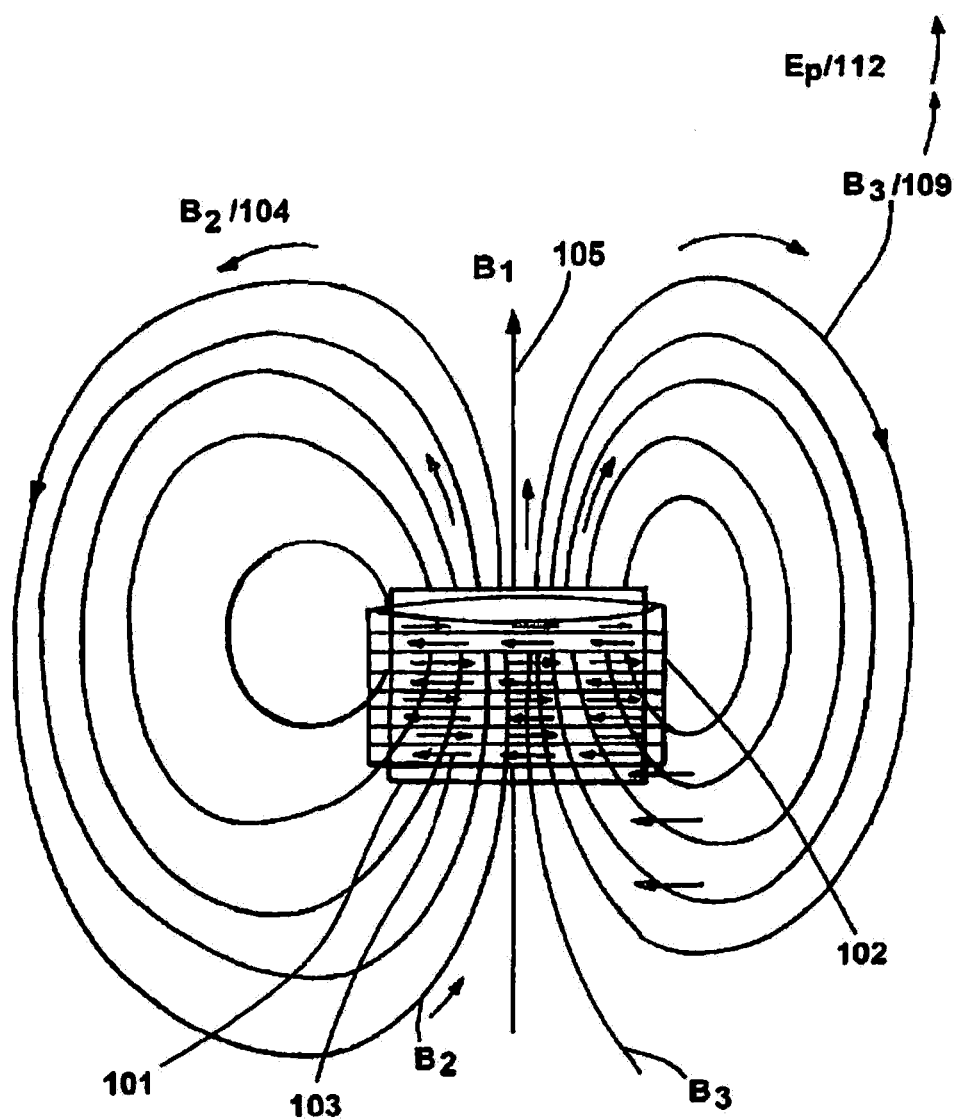
FIG. 8 is an enlarged schematic view of one of the inductive coil portions of the EMF probe assembly.

FIG. 8 illustrates a detailed view of the inductive coil 102 and its associated fields. Therein is shown the flow of current 103 within the coil 102, as well as radial field B1 and hemispherical fields B2 and B3.

Figure 6:
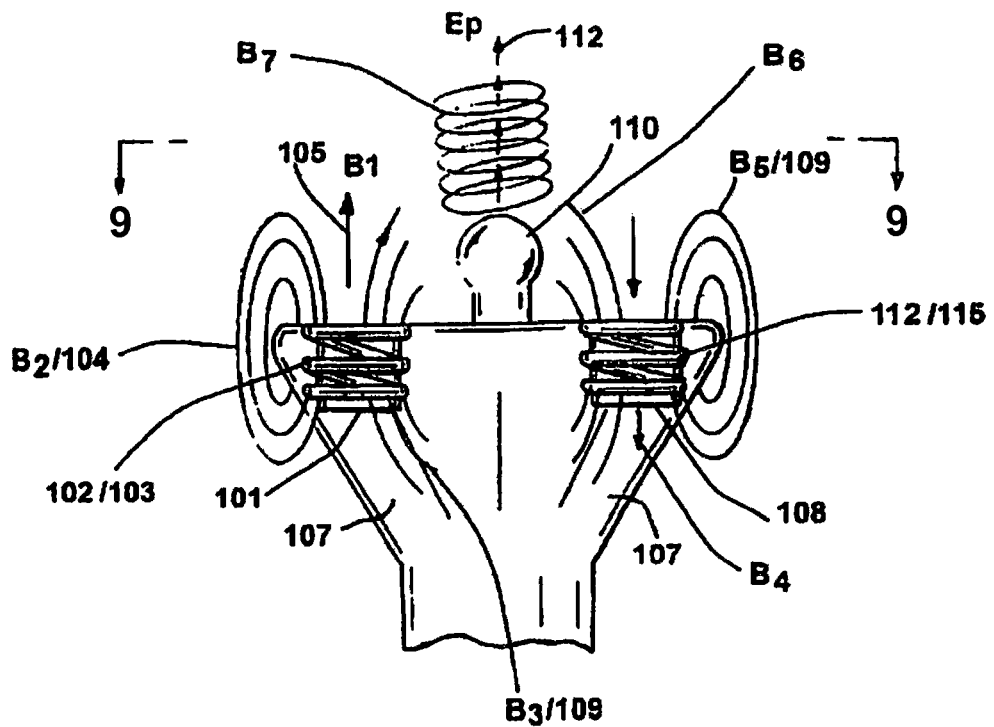
FIG. 6 is a side schematic view of an EMF probe assembly in accordance with the present invention.
Figure 7:
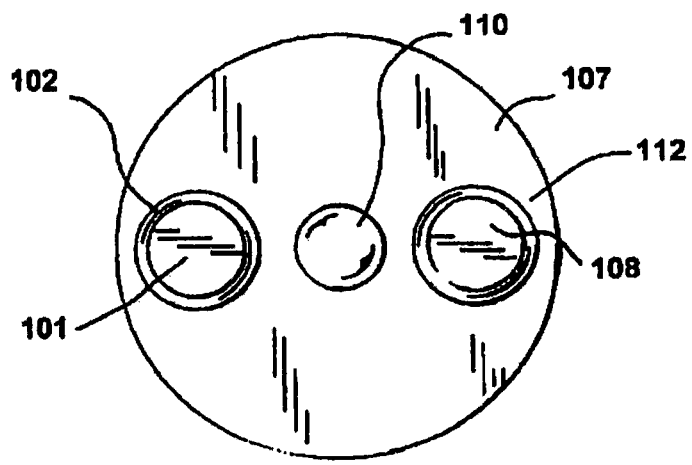
FIG. 7 is a top plan view of the assembly of FIG. 6.
Figure 9:
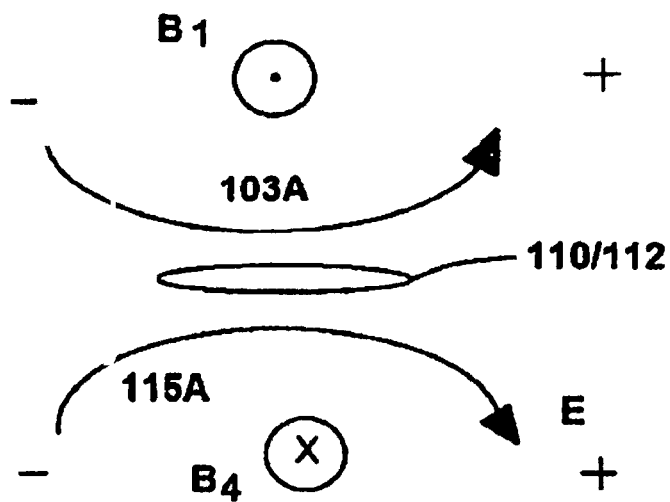
FIG. 9 is a top plan conceptual view taken along Line 4-4 of FIG. 6 showing the manner in which concentric electric fields associated with the B1 and B4 fields of the respective coils 102 and 112 produce electrical reinforcement effects of E fields induced by the B fields.

FIG. 9 illustrates an alternate embodiment 201/212 of the coils and ferrite structure of the embodiments of FIGS. 6-8. This embodiment differs from that of the previous embodiment only in the number of coils in the inductors. Such a change in the number of coil turns will produce differences in the strength and geometry of resultant magnetic fields B1 to B6. FIG. 9 also shows the continuity between field B2 of coil 211 and field B6 of coil 212. Arrows inside the coils show the direction of current flow therein.

FIG. 9 is a top plan conceptual view taken along Line 9-9 of FIG. 6, this showing the manner in which magnetic fields B1 and B4 have a re-inforcing effect of their induced E fields 103A and 115A at outer edges of the magnetic fields B2 and B5, thereby increasing the effect of spherical probe 110, its pulsed electric field 112, and the spherical induced pulsed magnetic field B7 associated therewith (see FIG. 6).

Figure 10:
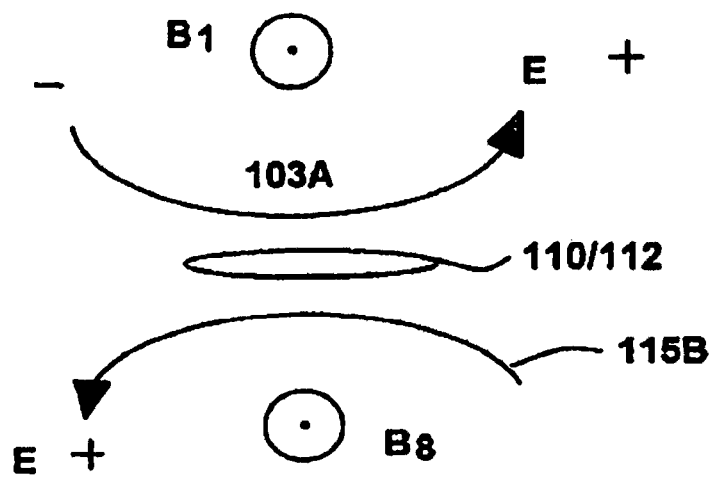
FIG. 10 is a view, similar to that of FIG. 9, however showing the manner in which the induced electric fields E associated with the axial magnetic fields B1 and B8 of the respective coils cancels each other if current is reversed through coil 112, reversing axial magnetic field B4.

Shown in FIG. 10 is a view in which the direction of current flow 103 within windings 112 about ferried core 108 (FIGS. 6 and 7) has been reversed such that the flow of current therein is in the same direction as that of coil 102 about ferrite core 101 at the left of probe 107 shown in FIGS. 6 and 7. When this is done, FIG. 10 indicates that a cancellation of the electric fields 103A and 115B responsive to magnetic fields B1 and B8. That is, magnetic fields B8 produce a cancelling electrical effect relative to the electrical field of B1. It is therefore, to be appreciated that the electromagnetic properties of treatment waves may be varied as a function of the directionality of current 103/115 which flow through coils 102 and 118 about the ferrite cores 108. See FIGS. 6 and 8. These current flows as to core 108 are shown as 115A in FIGS. 9 and 115B in FIG. 10.

Figure 11:
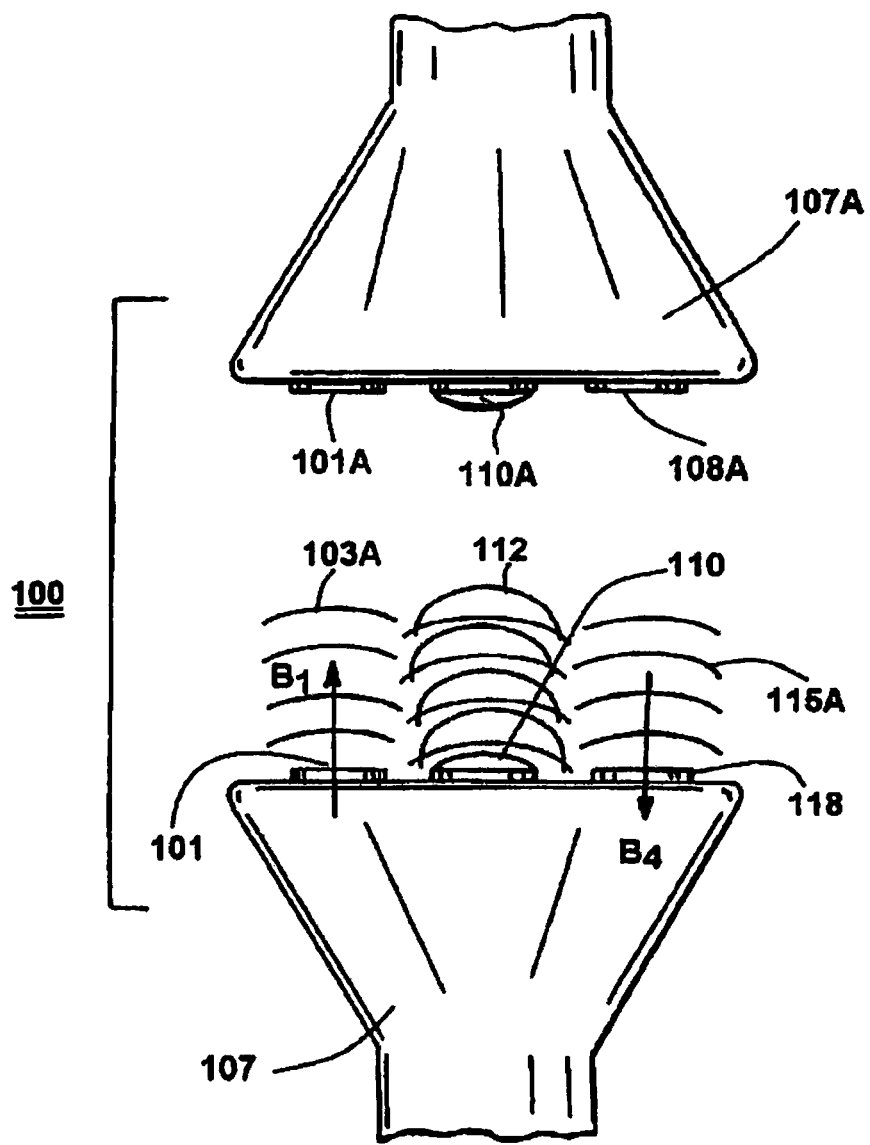
FIG. 11 is a view, similar to FIG. 6, however showing a complete treatment unit consisting of substantially identical upper and lower probes to those described in connection with said FIG. 6.

Shown in FIG. 11 is a view similar to that of FIG. 6, however showing that, in most applications, a second treatment probe 107A will also be used in system 100 which, generally, will be identical to that of lower probe 107. Use of two such probes is often necessary to locate and treat afflicted areas having a particular geometry, size or location.

Figure 12:
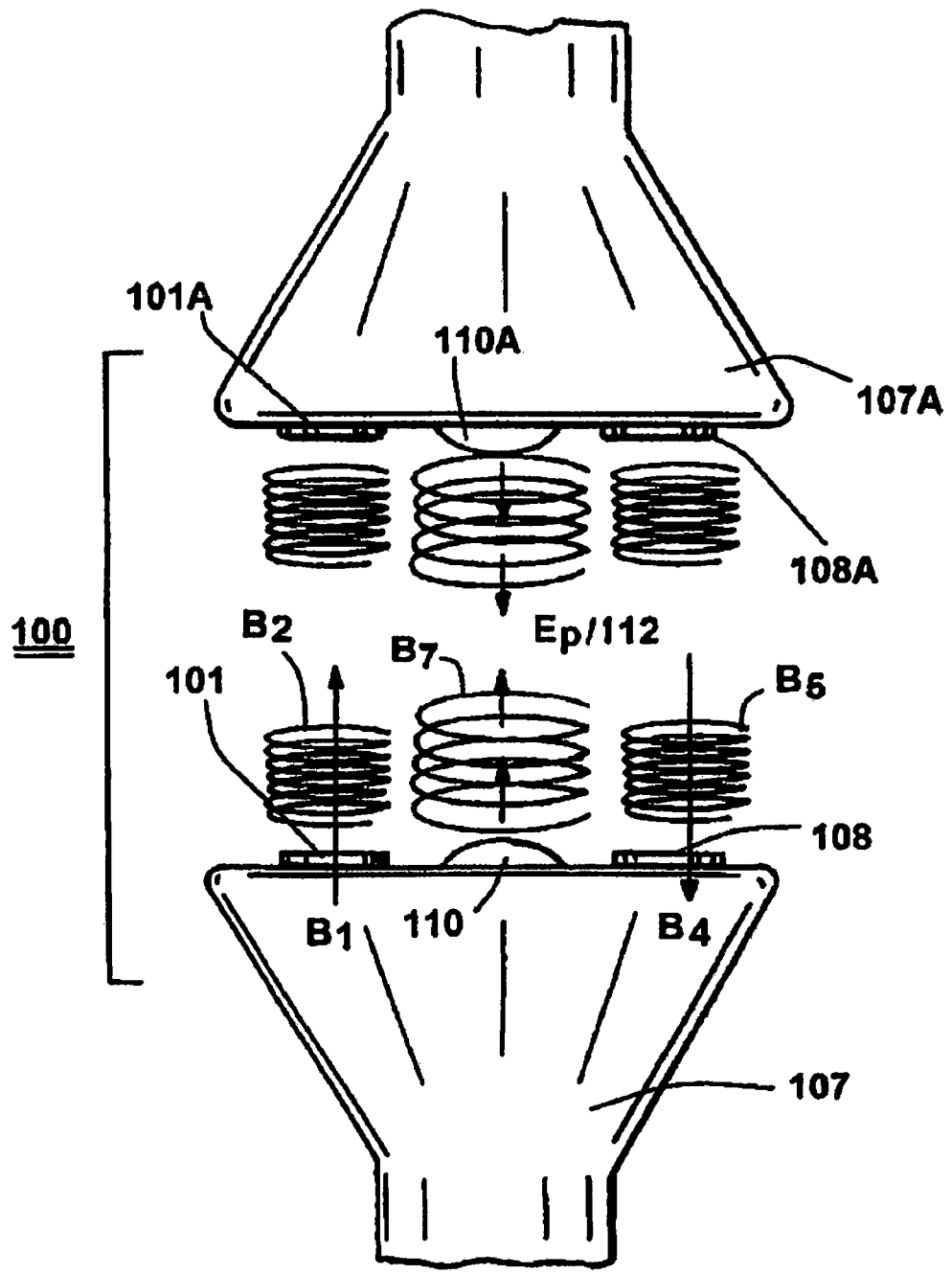
FIG. 12 is a view, similar to FIG. 11, however showing more details of the magnetic and electrical fields associated with the respective probes.
Figure 13:
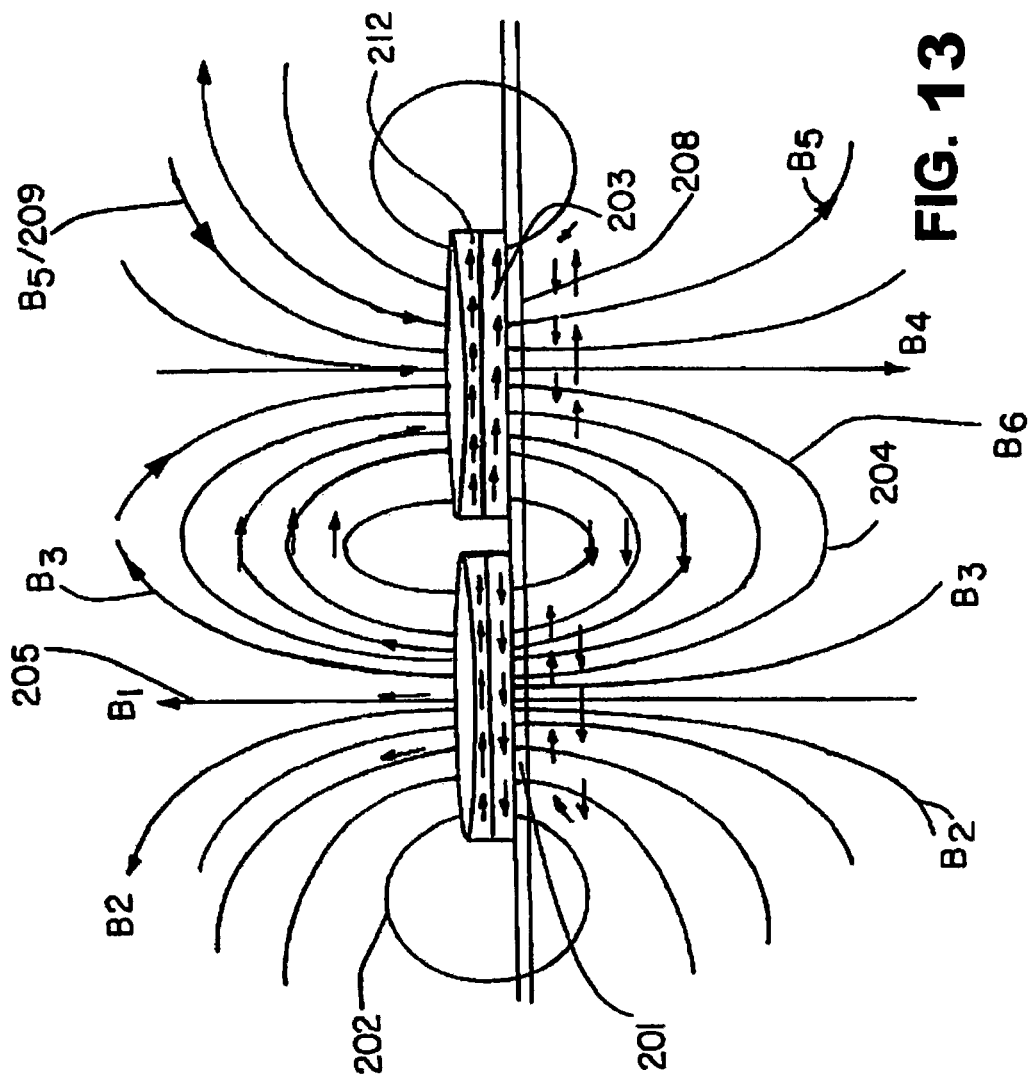
FIG. 13 is a schematic view of an alternative embodiment of the coil positioning and its assembly.

FIG. 12 is a view, similar to that of FIG. 11, however showing in more detail the electrical and magnetic fields associated with the present system.

Following direct physical administration of probe 110 to soft tissue, or neuronal cells, complex respectively transverse electrical and magnetic fields will be induced into the treated tissue. This is the case whether the patient suffers from inflammation, blood loss, neurologic damage, fibrosis, devascularization, or a variety of other conditions. All will respond in a manner very generally depicted by waveform 116/120 in FIG. 18. However, pattern segments 118 of low energy indicate a malfunction of the target tissue. Segments 120 indicate healthier cell function.

All waveforms are digitally converted to a histogram, chart recording and audio transfer for use by the system technician or clinician. Generally, the degree of unstable, static, randomness, or weakness of signal 116/118/120 is an indication of a degree of cellular or tissue level dysfunction of some type. Often, visual static will be expressed as a unstable and static sound in the audio transform. More particularly, if the waveform shown in FIG. 18 does not exhibit a particular degree of dysfunction, that will generally indicate to the technician that probes 107 and associated fields have not contacted the damaged or dysfunctional area of the tissue. In such case, the technician slowly positions and re-positions the probe until both the time domain and amplitude level of the unstable and static segment 118 is maximized. In a typical treatment scenario, when the probes 107 are correctly located at the cellular area most damaged or dysfunctional, retarded, unstable chart recording plots can be viewed and extreme and unstable static will be heard through the audio transform of signal 116/118/120. When the clinician hears such low amplitude and compressed time domain static, he will enhance the level of the applied signal 112 which becomes signals 401/408 in FIG. 19. This is the so-called treatment or healing signal of the present invention, the effectiveness of which is enhanced by the various magnetic fields B1 to B7, above discussed, as well as the cross-vector force associated with the interaction of electrical and magnetic fields projecting at right angle to each other. As such, the treatment of the invention is not simply unidirectional, or one defined by the directionality of EMF field Ep/112 (see FIG. 6) but, as well, by cross-directional magnetic and ExB forces which, it has been found, enhance healing and normalization of numerous dysfunctions including, without limitation, nerve bruises, soft tissue inflammation, including joint dysfunctions particular to arthritis. As such, the present therapy is invaluable in the treatment of much area which entails inflammation.

Macrophage invasion may be reversed as may fibroblast proliferation, permitting revascularization and the growing of healthy new tissue. Regarding to the duration of treatment at a given treatment site, the instant protocol is to apply and increase the signal 112 or 403 to the highest level which the patient can tolerate until the response train 116 (see FIG. 18) moves above the axis of stability indicating strength and stability. It has been found that after treatment with wave form 403 of FIG. 19, at the highest EMF level which the patient can tolerate, a return to normality of a particular tissue area treated, often occurs in a matter of just 10 to 15 seconds. The clinician then proceeds to locate other cells or tissue in the same area also associated with the malfunction. A few clusters of damaged cells will typically occupy a given treatment area. By searching for areas of unstable chart recording plots and unstable static, as above described, the technician is able to treat damaged tissue or associated neurons to promote both healing of soft tissue and of nerve fibers. It has been found that a patient, treated three times a week for a period of about three weeks can experience a cumulative and substantially and permanent relief from a wide range of soft tissue and nerve-related dysfunctions.

It is to be appreciated that a goal of the present therapy is to normalize the components of the apparently random static signal (referenced above) by normalizing each of the constituent levels of dysfunction through the use of selective E and B fields, pulses and waveforms. These produce induced currents, voltages and ExB forces in the tissue to be treated across the cell membranes of the treated tissue. The pulsed fields generated by the spherical probe 110 and particularly the axial E field 112 component emitted by it has its greatest effect at the macro or tissue level.

The alternating B fields produced by the two lateral coils 102 and 112 will, under Faraday's Law, induce low level alternating E fields that will reach across the air gap (the height of the probe 110) to cells of the target tissue, or between probes. See FIG. 11. These low level E fields, in the millivolt range, affect the action potential of the ionic channels (some of which are paramagnetic), e.g., channels of the nociceptive neurons, thus causing these channels to expel sodium anions to the outside of the cell. Excessive intracellular sodium is a source of pain and inflammation. The low level E field will, it is believed, also help to open the calcium anion channels by increasing the millivolt level action potential of those channels, triggering an inflow of calcium anions, which effect also causes a K anion inflow to the cell. As such, a proper balance of sodium, calcium and potassium anions between the intra- and extra-cellular fluid is accomplished, reducing pain and inflammation.

Calcium anions are also a known second messenger of many cell functions. Thereby, normalizing the intra-to-extra cellular balance of calcium anions to normalize the second messenger functions thereof.

The mechanism of operation of the ExB vector force is most likely that of a micro-vibration that operates as a micro-massage that helps to eject toxins from the target tissue.

Figure 17:
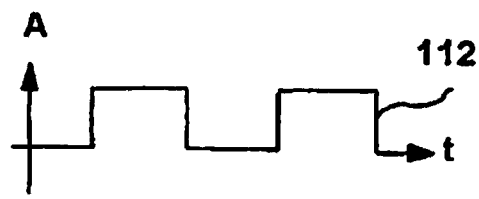
FIG. 17 is a view of AC EMF pulse packets emitted by the spherical probe of the assembly to locate a source of cell dysfunction.
Figure 18:
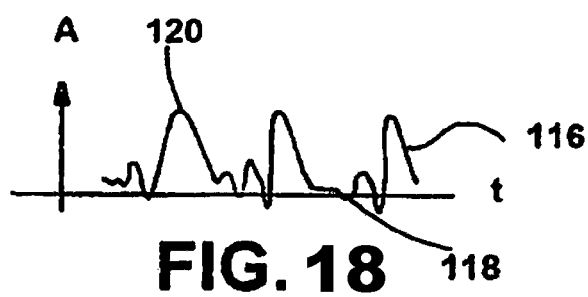
FIG. 18 is a view of pulse packets emitted by damaged tissue at initiation of treatment.

Shown in FIG. 17 is a waveform of a type used during initial probe emission 112, that is, when searching for a source of dysfunction. FIG. 18 shows a waveform that is received when a source of dysfunction is located responsive to waveform of an initial probe emission by the same electrode. The waveform typical of the type used at the start of treatment indicates a cell health positive response 112. However, 116 and 118 are health negative responses. The waveform of FIG. 19 is an algorithm simplified version of the waveform of FIG. 18. It includes a lower portion 401 (health negative) and upper portion 403 (health positive) which, it is to be appreciated, may be adapted in shape, dependent upon the needs of a technician to better locate somatic treatment points, such as area 403.

Figure 20:
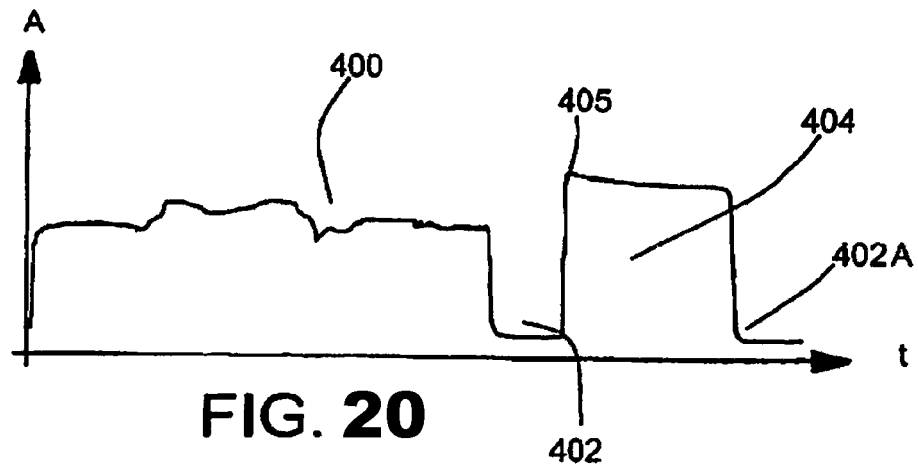
FIG. 20 shows an analysis based responsive waveform of a first target tissue locus responsive to the treatment signal of the type of FIG. 19.

FIG. 20 is a waveform of an initial responsive following the beginning of treatment at a target site. Shown is the amplitude of a weaker segment 100 of the responsive wave, followed by transition 102 to a second segment 104 of the responsive waveform, which is a stronger or healthier response, which is followed by a further transition 103 at the right of FIG. 20. Edge 105 of waveform 104 is indicative of a higher capacitance of the part of the cell of the target site.

Figure 21:
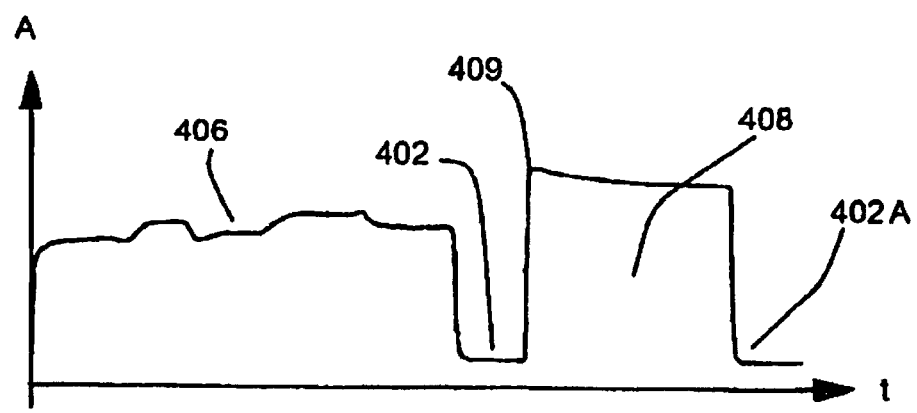
FIG. 21 is the view of a waveform, sequential to that of FIG. 20, however showing changes in the responsive waveform at the first locus of treatment resultant of application of electrical and magnetic fields produced by the probes shown in FIGS. 6, 12 and 13.

FIG. 21 is a view, sequential to that of FIG. 20, showing the result of initial treatment at a first site. Therein is shown that the amplitude of segment and shape of segment 100 of FIG. 20 has now increased to segment 106 of FIG. 21. This increased height waveform, as well as increased uniformity of the geometry of the waveform 106 is indicative of an induced healing process. Further is an area in which the portion 104 of FIG. 20 has changed to segment 108 shown in FIG. 21. Both segments 106 and 108 are indicative of a greater duration and length which correlates to healing at the site. Also shown is edge 109. The reduction in sharpness of edge 109 of segment 108 of the waveform indicates healing relative to the edge 105 in segment 104 of the waveform of FIG. 20.

Figure 22:
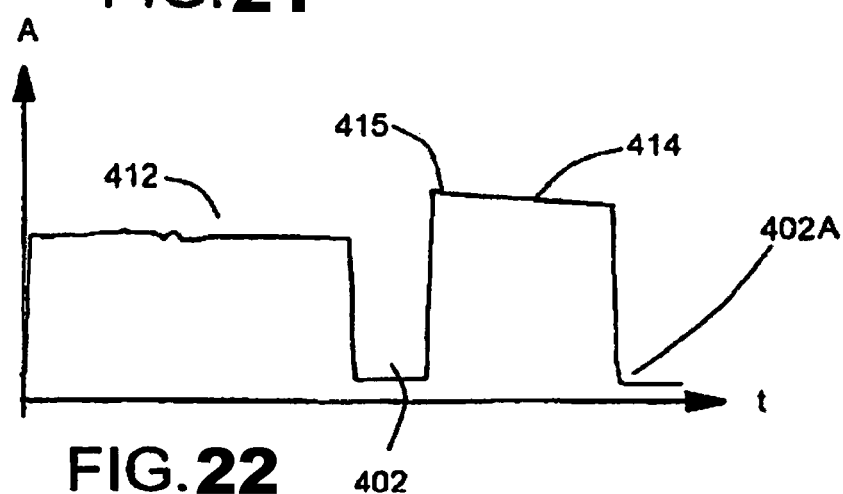
FIG. 22 shows a waveform similar to that of FIGS. 20 and 21 however at a time later in the treatment process.

FIG. 22 is a view at a second locus treatment of the spine showing that the treatment site exhibits a static-like and irregular segment 110 followed by a stronger segment 112 exhibiting a higher capacitance area 113. At 102 is shown a transition between segments.

Figure 14:
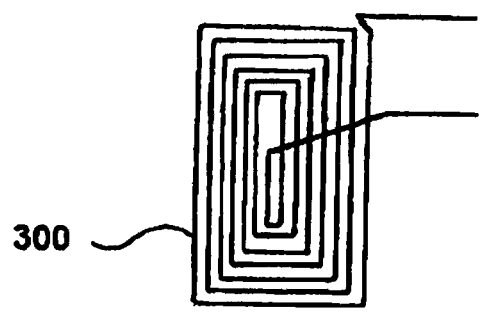
FIG. 14 is a schematic view of another embodiment of the coil portion of the system.
Figure 23:
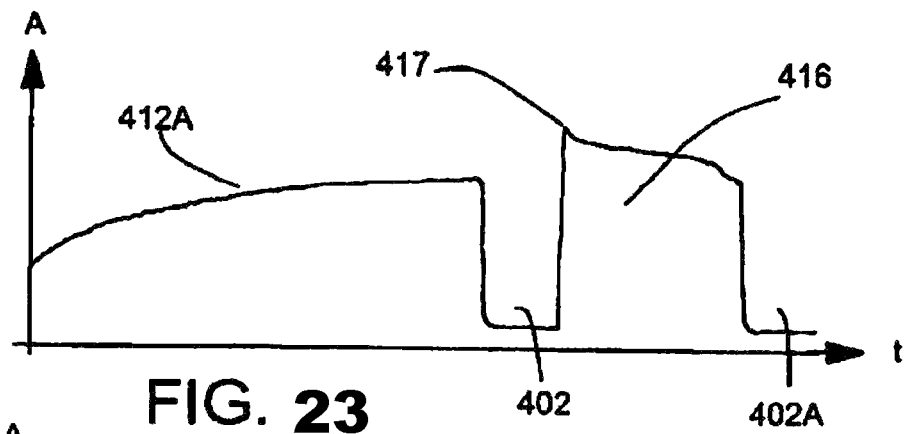
FIG. 23 shows a waveform sequential to that shown in FIG. 22.

FIG. 23 is another view of the second locus of treatment within the same general therapy area. A similar pattern of static followed by a healthier area 116 is observed both upon waveforms and in an audio transform thereof (unstable static sound versus a stable smooth sound). The treatment probe is moved slightly until an area of malfunction appears visually as an unstable weak signal and, in audio, as an unstable and static sound. After a period of application of complex EM wave and energy patterns, a more positive response may be seen in FIG. 14 as much healthier segments 118 and 120, with capacitative edge 121 upon segment 120.

Figure 24:
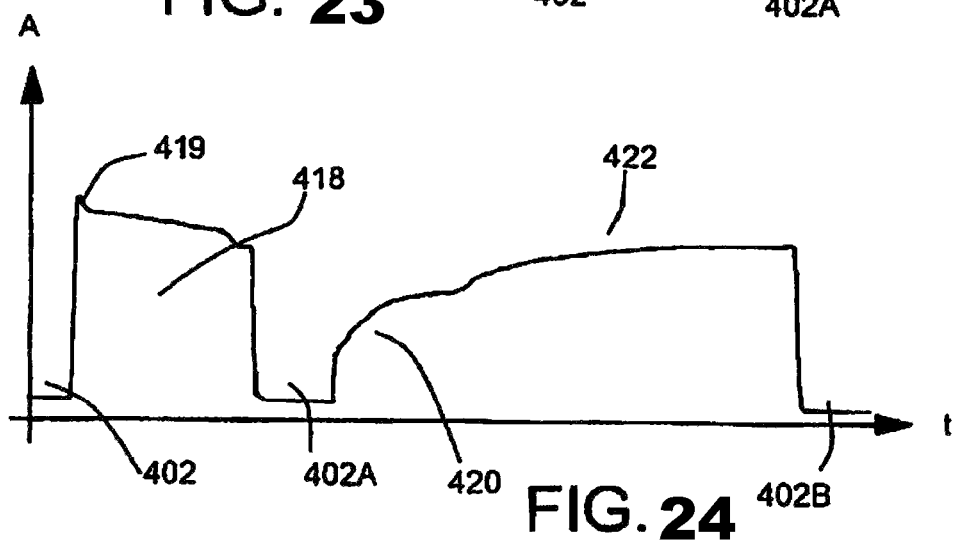
FIG. 24 is a view of a waveform at a second locus of the treatment site.
Figure 25:
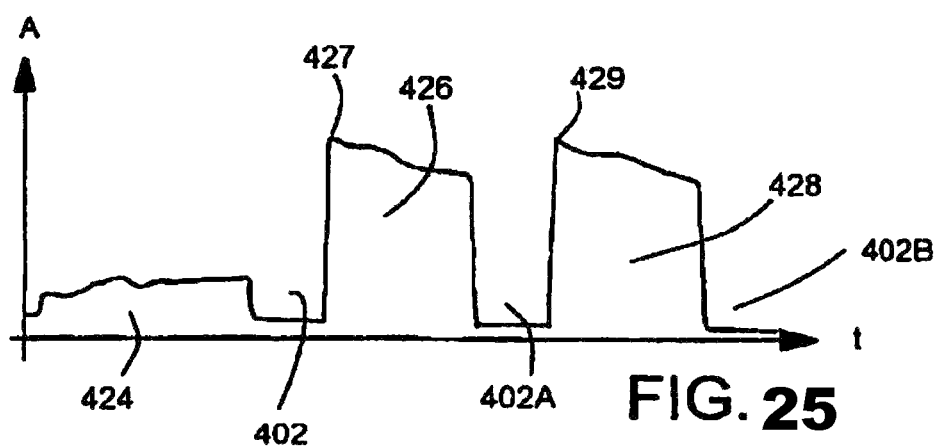
FIG. 25 is a view sequential to that of FIG. 24 showing further changes in the responsive waveform at the second locus of treatment.
Figure 26:
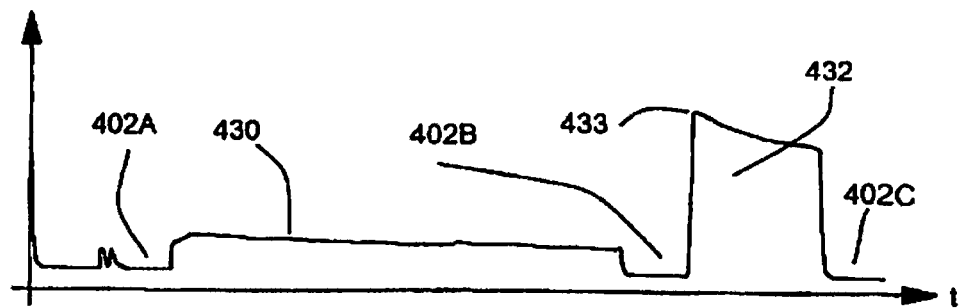
FIG. 26 is a waveform showing an initial response at a third locus of treatment associated with the same pain or tissue dysfunction.
Figure 27:
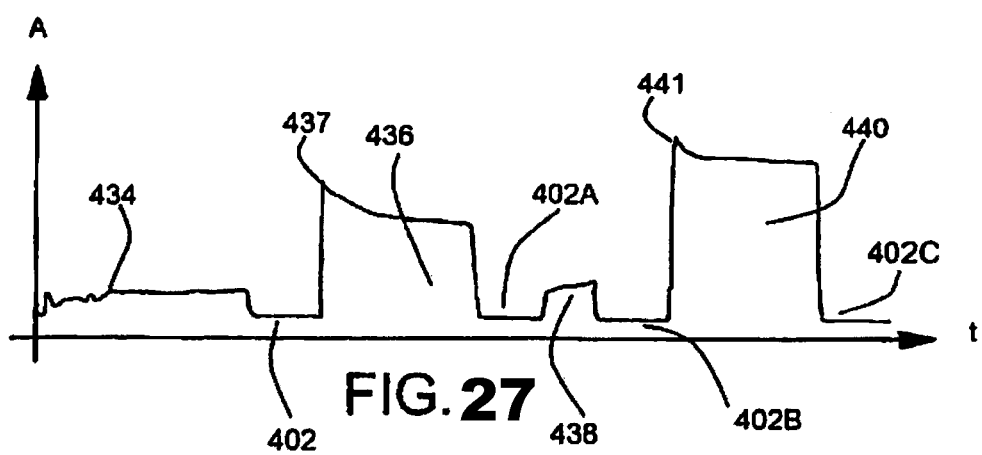
FIG. 27 is a view, sequential to that of FIG. 26, showing changes in tissue response to the treatment.

FIG. 25 is a waveform sequential to that of FIG. 24 in which segment 118 of FIG. 24 may be seen to be slightly changed into waveforms 122 and 124. However, segment 118 of FIG. 24 has now strengthened into a healthier waveform segment 122. Note greater the height of segment 122 versus 118. Pointed edge 125 shown in FIG. 25, is indicative of rate of change of capacitance at a treatment site, which is not desirable. Thus the waveform of FIG. 25 shows general strengthening with, however, a loss in length of the segment and a sharper edge 125 to waveform 124. Repetitive treatments of about ten minutes are needed to maximize all parameters.

Figure 15:
FIG. 15 is a flow diagram showing the manner in which the complex energy fields shown in FIGS. 8 and 13 when applied to a target tissue may be used to create three-dimensional images relative to the ionic functions of the treated cells.

FIG. 15 is a block diagrammatic view showing how, by the input of a complex electrical and magnetic signals to a tissue site of interest, a three-dimensional image based upon a map of any selectable two of the parameters (versus time) may be accomplished, including signal stability or rate of change in amplitude of signals. One may also calculate the first or second derivative of absolute signal amplitude as a more precise measure of signal stability. Capacitance is a further parameter that may be mapped against time to show how the effects of the treatment signal are retained at the treatment site. The derivative of capacitance may be mapped to show the rate of discharge of capacitance. Also, voltage across the cell membrane at the treatment site may, as in the view of FIGS. 2-5, be used as an important parameter, in combination with others, to produce two or three dimensional imaging of value to the treating technician and physician. The rate of change of voltage across cell membrane is also an important parameter which may be mapped both to provide a more complete picture of a user dysfunction and the result which the present therapy is effecting during treatment and between treatment session. An example of useful parameters which may be mapped in three-dimensions is shown in FIG. 17.

Figure 28:
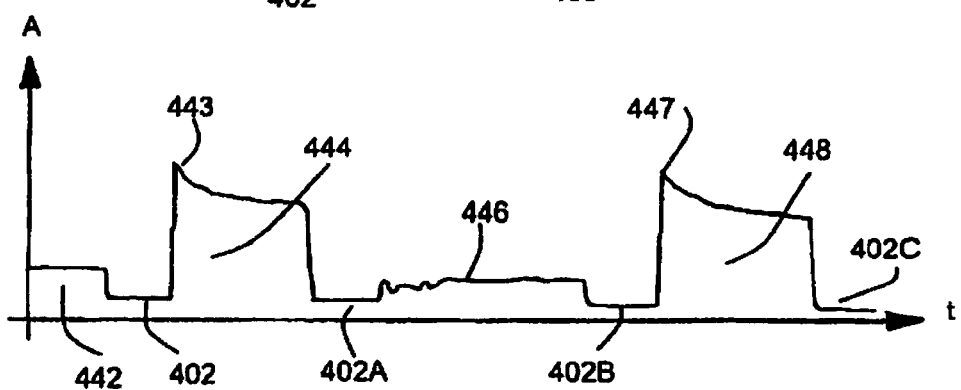
FIG. 28 is a view, sequential to that of FIG. 27, showing further changes at locus three of the treatment site.

Shown in FIG. 28 are illustrations of the manner in which the above-described electrical stimulations to the spine may be effected through the use of probe-embedded pads or patches 420 selectably applied to the pancreas 424, liver or large quad muscles, and pads applied to the kidneys for purposes of treatment of the kidneys.

Such electrodes 420 may be applied to the lower back near T4 for relief of hypertension.

Figure 29:
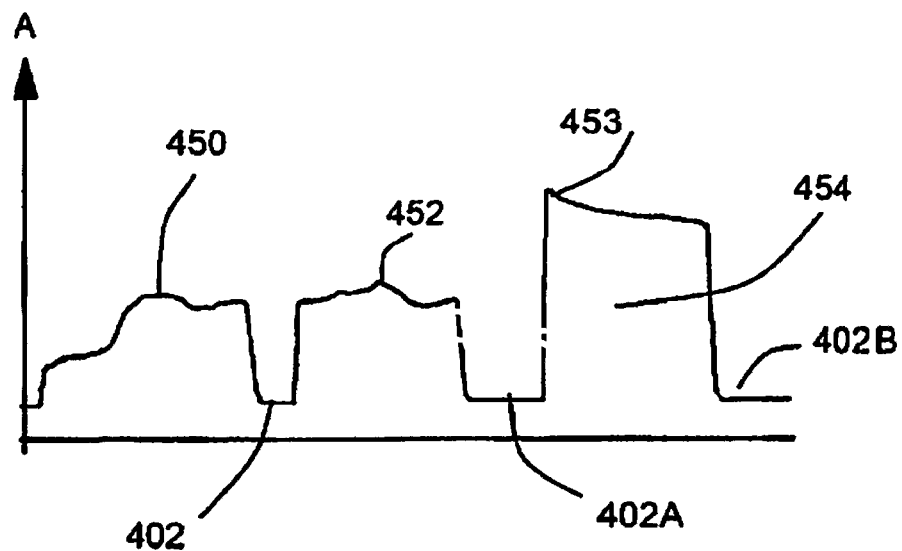
FIG. 29 is a view, sequential to that of FIG. 28 showing yet further changes in the responsive waveform at the third locus site.

FIG. 29 is a view, sequential to that of FIG. 28 showing responsiveness to the treatment signal in the form of increased average amplitude, this indicative of increased ion flow through the channels of cells at the tissue of interest. More particularly, segment 446 of FIG. 28 has strengthened into a healthier response 452 shown in FIG. 22. Segment 448 of FIG. 28 has also strengthened into segment 454 of FIG. 29

Figure 30:
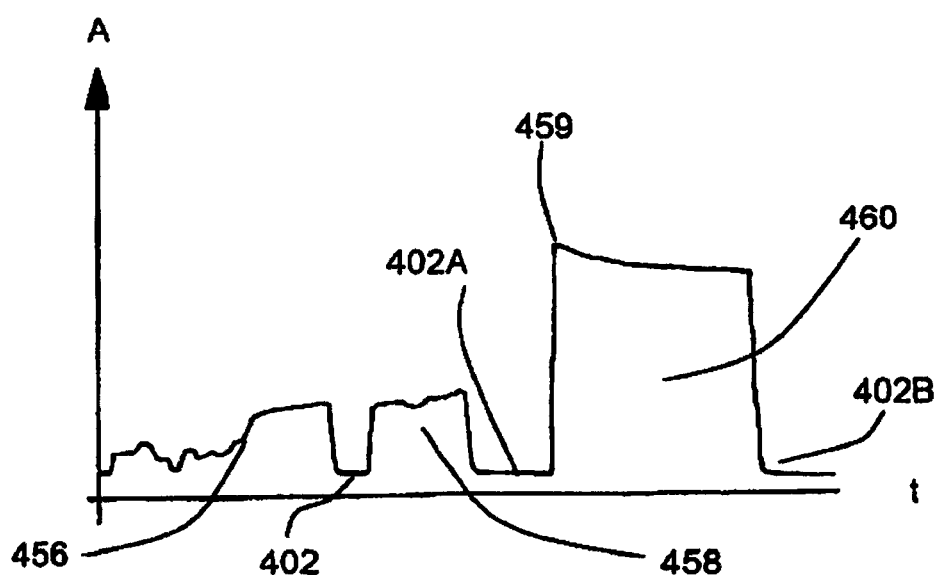
FIG. 30 is a view, sequential to that of FIG. 29 showing the responsive waveform at the third site of treatment.

FIG. 30 is a view, sequential to that of FIG. 29, showing that the signal segments 450 and 452 of FIG. 29 are unable to hold the healing effect of the applied signal while segment 454 is able to do so over a longer period, morphing into segment 460 while the edge 459 thereof is less acute than that of edge 453 of segment 454 of FIG. 29, this indicating that the therapeutic effect of the applied signal is holding at the cell grouping between transitions 402 and 402A in FIGS. 29 and 30 respectively.

From the above, it may be seen that the instant invention may be practiced through the use of an EMF electrode pad or probe assembly for the treatment and recognition of abnormalities including membrane flow of ions of cells associated with such conditions. Such an assembly includes probe 117; at least one ferro-magnetic core 101 positioned within said probe or pad; and at least one induction coil 112 wound about at least one core. An assembly will typically include a plurality of probes and a corresponding plurality of coils thereabout in which at least one of said cores includes sphere 110 integral to a core at a distal end. An electrical pulse train is furnished to a proximal end of at least one of said coils wherein a pulsed magnetic wave is thereby provided along an axis of said cores to the distal ends thereof. Such electrical pulse train therefore generates pulsed magnetic fields axial to said cores and extending as magnetic outputs from the distal ends of the probes. More than one, and preferably two probes are used concurrently such that two geometries of pulsed magnetic fields are emitted from sides or distal ends thereof. Typically one of such probes 110 would be the above-described probe having a spherical end while the other probe 101 or 108 would be a non-spherical probe. As may be appreciated, the use of said sphere is useful in generating magnetic field outputs of the probes having a hemispherical geometry.

As is above noted with respect to FIG. 31, sympathetic nervous system (SNS) is a branch of autonomic nervous system of the central nervous system and is related to the parasympathetic nervous system (PNS). The SNS, shown at the left of FIG. 31, operates through a series of interconnected neurons. Sympathetic neurons are frequently considered a part of the PNS, although many aspects lies within the central nervous system. SNS neurons of the spinal cord communicate with PNS neurons through a series of sympathetic ganglia. For purposes of the present invention, the central nervous system may be viewed as consisting of a spinal cord 10 and said SNS 12.

The PNS 14 is shown to the right of FIG. 31. The PNS is considered an automatic regulation system, that is, one which operates without the intervention of conscious thought. As such, fibers of the PNS innervate tissue in almost every organ, providing a regulatory function to areas as diverse regions of the eye, gut motility and urinary output of the body.

Certain groups of vertebrae, including the groups emanating from thoracic vertebrae T6 or T12 reach celiac ganglia 28 before dispersing to various internal organs in the thoracic region of the body including pancreas 24. From these internal organs occur a flow of axons of respective nerves at the base of the PNS to the Vegas nerve 30, shown in FIG. 31, and therefrom to other organs.

To reach target organs and glands, axions must travel considerable distances in the body and, to accomplish this, many axons relay their messages to second messages cells through synaptic transmission. This entails the use of a neurotransmitter across what is termed the synaptic cleft which activates further cells known as post-synaptic clefts. Therefrom a neuron message is carried to the final destination in the target organ or tissue.

Figure 19:
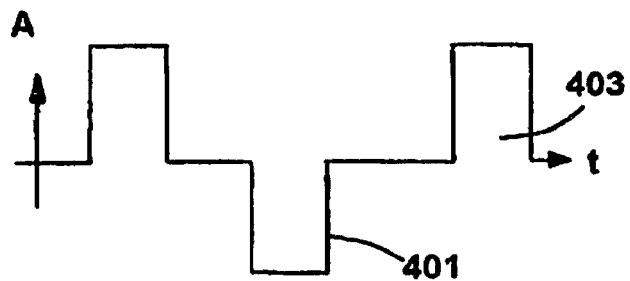
FIG. 19 is a view of representative pulse packets emitted by the spherical probe, used at the initiation of a treatment process.

A first step is typically the generation of a countervailing, correcting or inverse waveform or inverse EMR spectra which is the generation of an opposite magnetic single pattern from a dysfunctional signal that shown in FIGS. 18 and 19. The application of this inverse, countervailing or correcting pattern, has a pulse width modulation (PWM) process imposed upon a "sick" signal of the abnormal tissue is shown in FIG. 18. Thereby the system generates and applies to such tissue, a waveform of EMR peak spectra substantially inverse to that of out-of-phase resonances of said tissue signal to thereby increase or nullify peaks of the signal associated with abnormalities.

It is believed that the mechanism of action of the present invention is believed to encompass regulation of sodium, calcium, and potassium paramagnetic ions in the neuron membrane. Paramagnetic ions react to external electromagnetic energy just as a needle of a compass reacts to an external magnetic field. By diagnosing an affected area and modulating the electromagnetic treatment output to the affected area, chaotic paramagnetic ions will transform from a state of chaos to more orderly movement. This will improve and normalize neuron function, reducing pain and improving function of the nerves and affected tissue.

Figure 32:
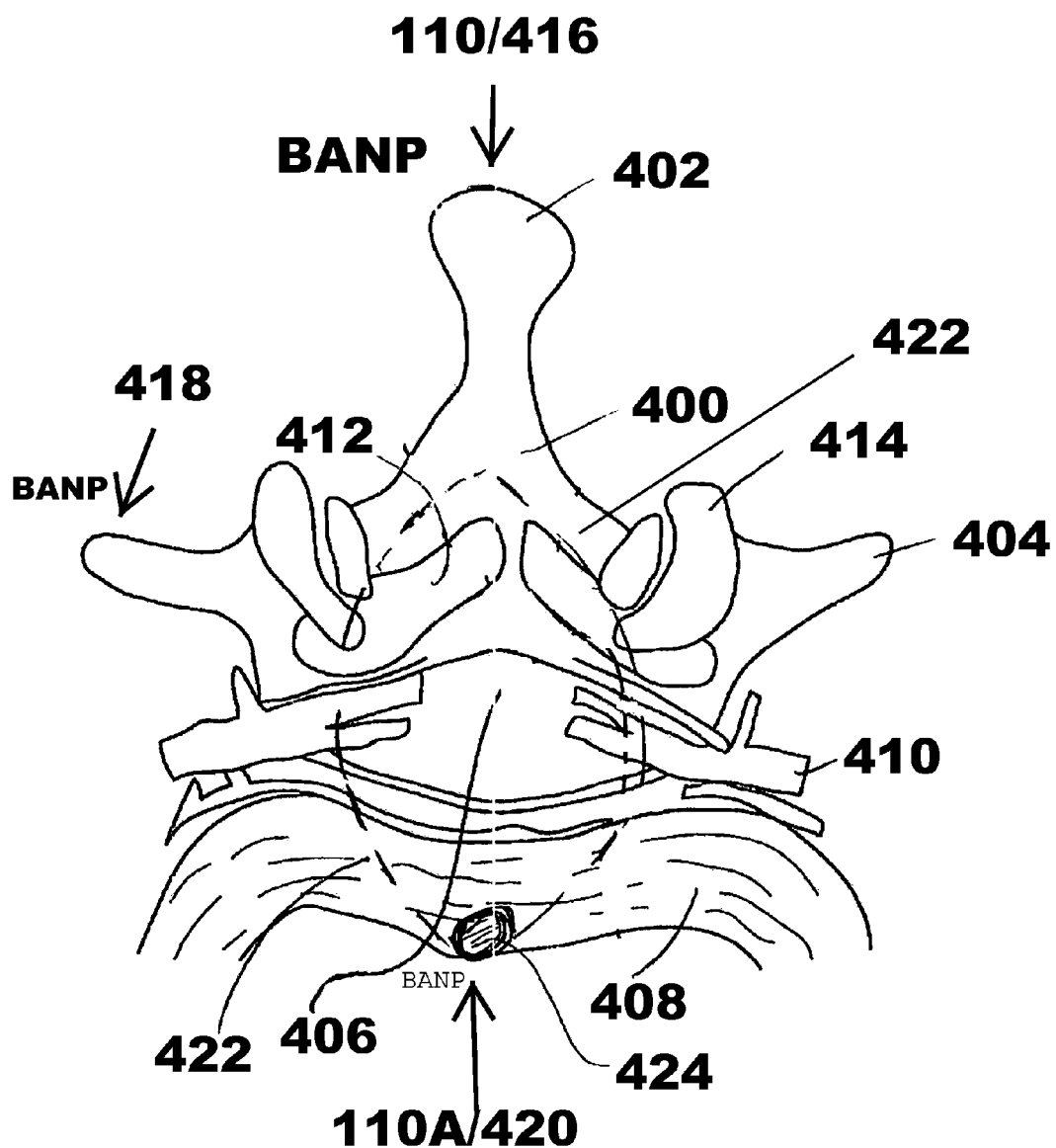
FIG. 32 is a schematic cross-sectional view of the spinal cord at the T7 vertebrae, and sites at which first and second electrodes may be applied.

In FIG. 32 is taken a transverse cross-section of the spinal cord at the T7 thoracic vertebrae, indicated as vertebrae 400 in FIG. 32. Also shown therein is a sharp dorsal projection of the vertebrae known as spinal apophysis 402. At the lateral sides of vertebrae 400 are transverse apophases 404. At the centermost area of the vertebrae, known as foramen magnum 406, are most of the nerve bundles that carry information to and from the brain and the extremities. The abdomen side of the T7 vertebrae area is indicted as reference numeral 408. Elements 410 shown in FIG. 32 are known as the pediculae of the vertebrae, and elements 412 and 414 indicate interlocking upper projections from vertebra T8 which is situated immediately below vertebrae T7.

Further shown in FIG. 32 are a potential BANP location 416 at which an associated electrodes 416 is applied. However, in a given case, a preferred BANP of a vertebrae may exist at the transverse apophysis 404 such that one electrode of the present system would be applied in the area of the transverse apophysis of the vertebrae, such electrode constituting the above referenced one sphere 110 including a means for measurement of bioreactance of a tissue or organ to be treated by the monitoring of bioreactive parameters associated with electromagnetic parameters received at said point. A suitable means for measurement of such bioreactance is taught in General Electric U.S. Pat. No. 8,542,023, although many less sophisticated means or instruments are known in the art for the measurement of reactance and its components, such as the product of General Radio-Hazeltine. Many such devices also appear in the patent literature, such as Bell Labs, U.S. Pat. No. 4,419,623 and its progeny.

In FIG. 32, shown oppositely to the location of the electrode 416 is electrode 420 which, to the extent possible, is placed upon the abdomen of the patient in a location at or close to the organ or tissue to be treated, for example, in the case of treatment of diabetes, the pancreas. This, in other words, constitutes the above-referenced means for neurologically transmitting second bioactive parameters at the BNP of an organ or tissue to be treated, that is, parameters modify discreet reactive values responsive to those measured by said first electrode 110/416 and second electrode 110A/420 which values, as above described, are received and transmitted responsive to abnormal reactive waveforms received from an organ or tissue to be treated. See FIG. 12.

A variety of strategies may be employed to quantify and measure useful second bioreactive parameters inclusive of the systems described above as well as the various algorithms and artificial intelligence approaches as described below. In essence, the present system comprises a means for receiving and transmitting, through both electrodes 416/418 and 420, within the PNS or SNS nerve pathways shown by dotted lines 422 in FIG. 32. Return signals may heuristically modeled from cell disorders appearing as inputs of particular voltage and capacitance gradients related to ion motility across membranes of cells of an afflicted tissue. That is, the system employs means for selection of suitably responsive transmissive parameters responsive to received signals at BANPs of interest. Stated otherwise, the electrodes 416/418 and 420 are usable both as a measurement means of the present electrotherapeutic treatment system and as a means for transmitting corrective bioreactive parameters. Dotted lines 422 in FIG. 32 indicates nerve pathway from the vertebral nerve outlet (BANP) 402/404 to electrode 420 which, as above noted, is located on abdomen 408 proximally to the organ or tissue of interest.

The RLC of the system employs various algorithms, starting with a so-called inverse, countervailing or correcting waveform of the injury tissue as a first order basis of treatment, this followed by robust stochastic models to generate appropriate stimuli profiles to enable the system to provide a sophisticated treatment or correction signal. Therein at least three models or algorithms are contemplated, these including the following: (1) sequential, adaptive self-learning method and implementation (for a single electrode pair); (2) block adaptive self-learning method and implementation (for an electrode array); (3) one and multi dimensional neural network-based controller algorithms; (4) sequential data autoregressive method and implementation (for a single electrode pair); and (5) block data autoregressive method and implementation (for an electrode array).

In addition, the filtering of a measurement module eliminates error signals which typically appear as waveform ripples, to thereby enable generation of a correction or treatment signal from a self-learning multi-electrode, thereby having enhanced efficacy in the cancellation of pain and, ultimately, long term treatment of the condition of interest.

Combinations of algorithms may be employed to generate interchannel waveform correlations to ensure convergence of the model analysis and promotion of its learning curve for the modeling of the tissue injury, treatment profiles and peak resonances associated therewith.

In summary, the technology employs a frequencies of 1 Hertz to 1 G hertz, and low gauss (0.1 to 4 Tesla) in treatment signals to increase, decrease, flatten nullify out or modify of phase resonance peaks of a measured waveform of the tissue to be treated. Similarly, the correction or treatment signal which is applied to treat the abnormal tissue signal obtained by the measurement module is intelligently developed by a self-learning multi-electrode PTU in which various heuristic algorithms are used to ensure convergence and efficient development of models necessary to optimize tissue profile, peak resonance codes, and the use of this information for effective therapy in an array of medical conditions. At higher frequencies the role of reactance in formulating corrective strategies will of course increase.

This technology also enables treatment of conditions such as arthritis, post surgical pain, post surgical reduction of swelling inflammation and bruising, Osgood Schlater Disease, treatment of organ transplant patients for the purpose of reducing organ rejection, adhesive capsilitus, MS, ALS, motor neuron disease, reduction of keloid scaring treatment of skin graft sites for better vasculasation and better chance of successful graft improvement of circulation and oxygen saturation in compromised tissue and limbs, limb and digit reattachment for better chance of successful graft, improvement and normalization of conductivity in infracted cardiac tissue, joint inflammation and injuries, fibromyalgia, reflex sympathetic dystrophy, neuralgia, peripheral neuropathy, macular degeneration, wounds and scleroderma. However, a library of tissue profiles and peak resonance codes may be employed in the system in the development of a separate library of profiles and EMR resonance codes for each patient and, also, as a baseline/or electromagnetic structures, of healthy tissue of many types, which might be employed in the generation of an inverse waveform or treatment purposes. Accordingly, my historic library of tissue profiles and peak resonance codes may be intergraded into the stochastic models, as set forth above, to generate appropriate stimuli profiles to enable a sophisticated treatment or correction signal. Therein a simple low-order low pass filtering process, to eliminate signal ripples, constitutes a starting point.

Resultingly, there is taught above an ion channel electromodulation system having applications across a broad range of conditions, as summarized below.

Figure 33:
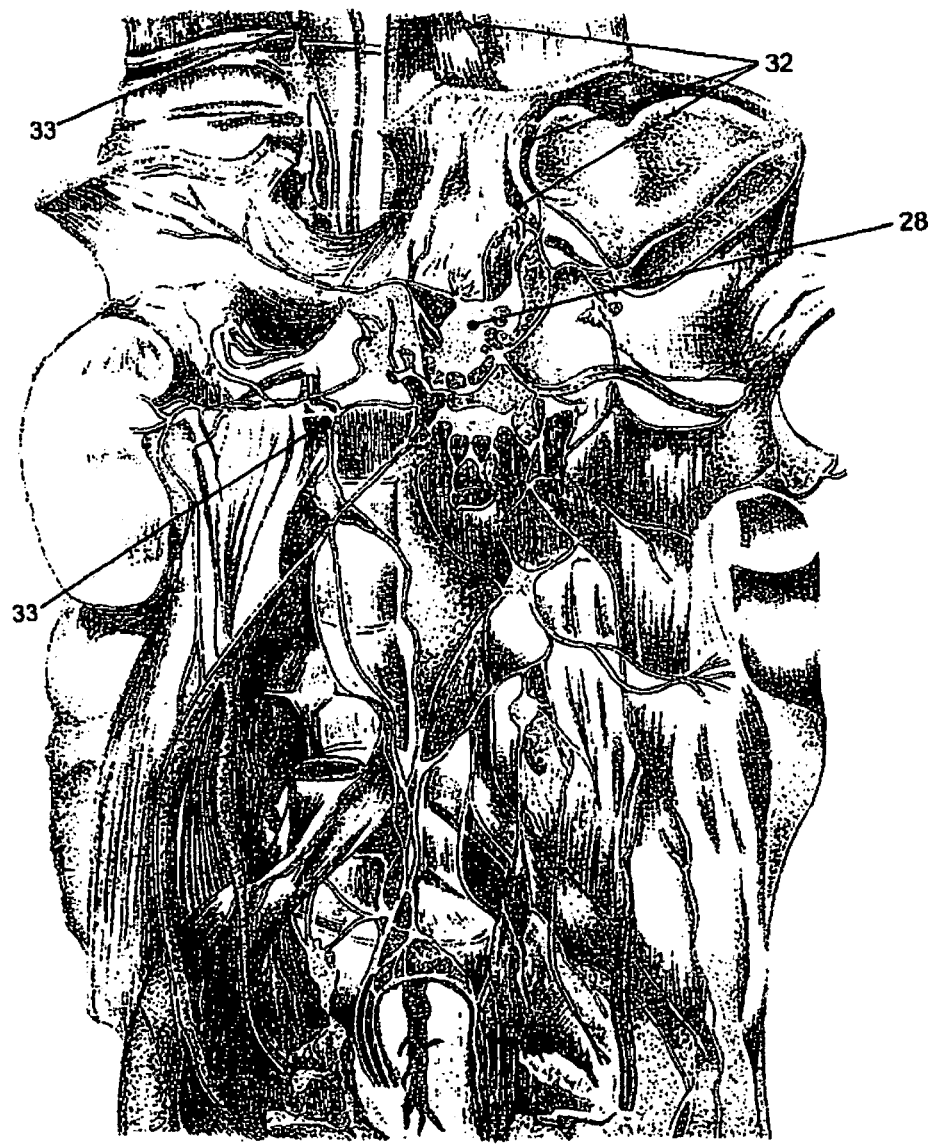
FIG. 33 is a schematic view of the abdomen at sites where a second electrode may be applied.

Shown in FIG. 33 are sample locations upon chest and the abdomen at which electrode 420 may be placed that are readable through the SNS or PNS.

In accordance with the medical principles of treatment discussed above, the pulsed magnetic field output of the probes is preferably of an opposing electron-magnetic polarity to that generated by abnormal tissue to be treated. Thus provided is a system for generating a pulsed electromagnetic field, at a distal end of the at least one of said probes, having a countervailing electro-magnetic geometry to that generated by an abnormal flow of electrons across said cell membranes of a given tissue.

Figure 16:
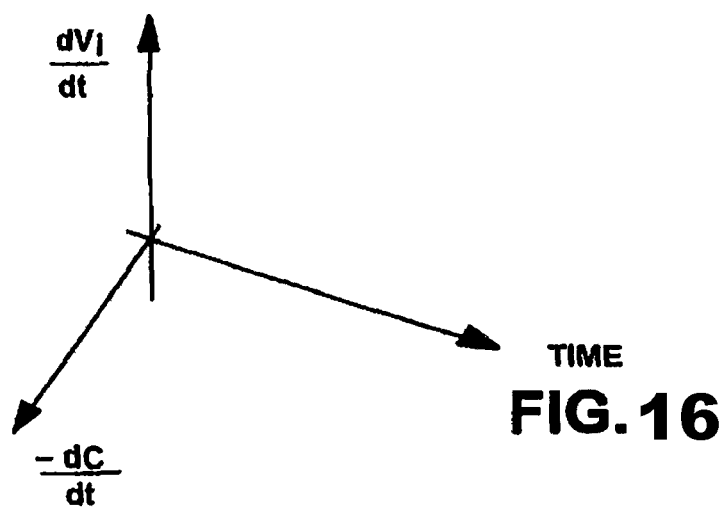
FIG. 16 is a conceptual view of parameters which may be visually displayed to form a three dimensional image which relates to the velocity of anion transport function of cells of the target tissue and rate of capacitative change at the target tissue. One map also maps voltage of ion transport at a treatment site and signal stability at treatment site in a three-dimensional format relative to the initial responsive signal data over the period of treatment.

The invention, as above described, also includes a histogram, chart recording plotting and an audio transform for expressing electro-magnetic changes and responses of abnormal cells and tissues into human audible frequencies. Using such tools and frequencies, one may adjust the magnitude and geometry of the above-described electro-magnetic field outputs of the probes. Histogram, chart recording and audio software recognition, as well as clinical training of technicians, enables one to recognize the meaning of the histogram, chart recording plots and human audible frequency outputs as correlating to desirable or undesirable voltage gradients shown in FIGS. 20-30 across cell membranes of cells of an afflicted tissue. Per FIGS. 5 and 16, visual means may, similarly, be provided for the viewing of the reactive parameters or electro-magnetic waveforms provided in the present therapy and by the afflicted tissue.

All patents and publications recited herein are incorporated herewith in their entirety.

Accordingly, while there has been shown and described the preferred embodiment of the invention is to be appreciated that the invention may be embodied otherwise than is herein specifically shown and described and, within said embodiment, certain changes may be made in the form and arrangement of the parts without departing from the underlying ideas or principles of this invention, as claimed herein.

The invention claimed is:

1. An electrotherapeutic treatment system, comprising:
   (a) at least one skin contact element including a first electrode for measurement of bioreactance at biologically active neurological points (BANP) of a tissue or organ to be treated, including monitoring of electromagnetic parameters received at said points and means for generating corrective parameters responsive to those measured;
   (b) a second electrode, situated on the abdomen proximally to a tissue or organ to be treated, for neurologically transmitting bioreactive parameters at said BANP of said tissues or organs, said parameters modifying discrete reactive values responsive to those measured by each of the said first and second electrodes responsive to abnormal parameters received from tissues or organs to be treated at said BANP,
   in which said first and second electrodes respectively comprise:

a first transmitting means proportioned for application to a dorsal surface of a spinal cord situated at vertebrae having a neurological association with an organ or tissue to be treated; and a second transmitting means positioned against a location upon an abdomen or other external area of a patient, said location physically proximal to a tissue or organ to be treated;

(c) at least one of said probes including a substantially spiral conductive core having an elongate axis and a flow of electrical current therethrough, said current producing a substantially concentric magnetic field about said axis of said conductive core, said probe emitting an axially projecting magnetic field at a distal end thereof to said BANP of said tissue or organ, said at least one probe defining at least one of said means for neurological transmission; and (d) an electrical pulse train applied at said end of a first probe emitting a pulsed magnetic field at an end of a first probe and said pulsed train also applied at a distal end of a second probe, parameters of each said pulsed magnetic fields responsive to abnormal bioreactive parameters and generating corrective parameters responsive to those abnormal parameters measured, said probes defining said first and second electrodes respectively.

2. The assembly as recited in claim 1, further comprising:
an audio transform, regarding electrical or electromagnetic changes in response to signals received from signals or fields transmitted into abnormal cells and organs, at human audible frequencies.

3. The system as recited in claim 2, in which:
said first and second electrodes each include means for measuring respective inductive and capacitive components of said bioreactive parameters.

4. The system as recited in claim 2, further comprising:
means for measurement of resistive components of said measured bioreactive parameters, said components definable relative to a selectable biocompatible voltage.

5. The system as recited in claim 2, in which each of said electrodes comprise:
at least one probe, each including a substantially linear conductive core having an elongate axis and a flow of electrical current therethrough, said current producing a substantially concentric magnetic field about said axis of said conductive core, said probe emitting an axially projecting electrical field at a distal end thereof to said BANP of said tissue or organ, said at least one probe defining at least one of said means for neurological transmission.

6. The assembly as recited in claim 2, further comprising means for adjusting the amplitude of respective transmitted waveforms in response to levels of audible frequencies received.

7. The assembly as recited in claim 2, in which said responsive signals received by said electrodes further comprise:
means for heuristically modeling cell disorders as a function of particular voltage and capacitative gradients of ion motility across membranes of cells of an afflicted tissue for selection of suitable responsive transmitted reactive signals by said electrodes at said BANP.

8. The system as recited in claim 1, in which:
said transmitted parameters comprise pulsed signals.

9. The system as recited in claim 1, in which said means for neurologically transmitting said bioreactive parameters comprise:
means for separately transmitting inductive, capacitative and resistive components thereof.

10. The system as recited in claim 1, in which:
parameters of said second transmitting means define a single EM waveform prior to transmission at said BANP to be targeted.

11. The system as recited in claim 10, comprising:
said second transmitting means of bioreactive parameters comprise a waveform of interlaced resistive and capacitative components.

12. The system as recited in claim 1, in which each of said electrodes comprise:
at least one probe, each including a substantially linear conductive core having an elongate axis and a flow of electrical current therethrough, said current producing a substantially concentric magnetic field about said axis of said conductive core, said probe emitting an axially projecting electrical field at a distal end thereof to said BANP of said tissue or organ, said at least one probe defining at least one of said means for neurological transmission.

13. The system as recited in claim 12, further comprising:
an induction coil wound about said core, the coil having an electric current passing between proximal and distal ends thereof, said coil generating a magnetic field between opposite poles of said core.

14. The system as recited in claim 13, in which said magnetic field generated between opposite poles of the core define a communication with said axially emitted electrical fields of said probe of said conductive element, producing an ExB vector at locations of intersection thereof at substantially right angles.

15. The system as recited in claim 14, in which at least one said core defines a partial sphere at a distal end of said core of said probe.

16. The system as recited in claim 14, in which said at least one said core includes a pivot point within a linear axis thereof by which an axis of said magnetic field thereof may be titled relative to said pivot point.

17. The system as recited in claim 12, in which said electrical field within said coil of said one core comprises:
an electrical pulsed train spirally furnished to a proximal end of one or more of said coils, a pulsed magnetic wave thereby provided along an axis of said core projecting about it and at a distal end thereof.

18. The system as recited in claim 1, in which said pulsed fields from the first and second probes modulate against each other and define field shapes and directions of combined first and second probe magnetic fields, a combination of first and second probe fields creating a third modulated field resulting from the combination of the first and second probe magnetic fields including modulation of fields created from interaction of diagnostic fields.

* * * * *